United States Patent [19]

Gray et al.

[11] Patent Number: 5,387,610
[45] Date of Patent: Feb. 7, 1995

[54] PEPTIDE DERIVATIVES OF COLLAGENASE INHIBITOR

[75] Inventors: Robert D. Gray; Arno F. Spatola; Krzysztof Darlak, all of Louisville, Ky.

[73] Assignee: Research Corporation Technologies, Inc., Tucson, Ariz.

[21] Appl. No.: 981,149

[22] Filed: Nov. 24, 1992

Related U.S. Application Data

[63] Continuation of Ser. No. 715,948, Jun. 14, 1991, abandoned.

[51] Int. Cl.$^6$ .................. A61K 37/02; A61K 31/195; C07C 259/10
[52] U.S. Cl. ...................... 514/575; 514/18; 514/507; 530/323; 530/330; 530/331; 562/623
[58] Field of Search ............... 530/323, 330, 331; 562/623; 514/575, 507, 18

[56] References Cited

U.S. PATENT DOCUMENTS

| | | | |
|---|---|---|---|
| 4,235,885 | 11/1980 | Sundeen et al. | 514/562 |
| 4,263,293 | 4/1981 | Sundeen et al. | 514/237.8 |
| 4,310,517 | 1/1982 | Etschenberg et al. | 514/17 |
| 4,595,700 | 6/1986 | Donald et al. | 514/616 |
| 4,599,361 | 7/1986 | Dickens et al. | 514/575 |
| 4,687,841 | 8/1987 | Spilburg et al. | 530/331 |
| 4,720,486 | 1/1988 | Spilburg et al. | 514/18 |
| 4,743,587 | 6/1988 | Dickens et al. | 514/587 |
| 4,771,038 | 9/1988 | Wolainin et al. | 514/18 |
| 5,114,953 | 5/1992 | Galardy et al. | 514/323 |

FOREIGN PATENT DOCUMENTS

| | | | |
|---|---|---|---|
| 0236872 | 2/1987 | European Pat. Off. | 530/331 |
| 0262053 | 9/1987 | European Pat. Off. | 514/575 |
| 0274453 | 1/1988 | European Pat. Off. | 514/575 |

OTHER PUBLICATIONS

Gray, et al. in *Biochemical and Biophysical Res. Comm.*, 101, 1251 (1981).
Gray, et al. *Inhibition of Porcine Synovial Collagenase by Thiol Peptides*, Tenth American Peptide Symposium, poster p-120 (1987).
Reich et al., Cancer Research,, vol. 48, No. 12, pp. 3307-3312 (1988).
Lelievre et al., Matrix, vol. 10, No. 5, pp. 292-299 (1979).
Chem. Abstracts, vol. 114 (No. 11) Abst. No. 114:97,241-n, Mar. 18, 1991.
Chem. Abstracts, vol. 109 (No. 9) Abst. No. 109:66422-q, Aug. 29, 1988.
Chem. Abstracts, vol. 106, (No. 25), 106:214,381f, Jun. 22, 1987.
Chem. Abstracts, vol. 105 (No. 17) 105:153550-r Oct. 27, 1986.

*Primary Examiner*—Alan L. Rotman
*Attorney, Agent, or Firm*—Scully, Scott, Murphy & Presser

[57] ABSTRACT

This invention is directed to a collagenase inhibitor of the formula:

$$R_7O-\underset{\underset{O}{|}}{\overset{H}{\underset{|}{N}}}-\underset{\underset{R}{|}}{C}-CH-\underset{\underset{R_1}{|}}{CH}-\overset{O}{\overset{||}{C}}-\overset{H}{\underset{|}{N}}-\overset{H}{\underset{\underset{R_2}{|}}{C^*}}-B-X-D$$

112 Claims, No Drawings

PEPTIDE DERIVATIVES OF COLLAGENASE INHIBITOR

This is a continuation of copending application Ser. No. 715,948, filed on Jun. 14, 1991, abandoned.

BACKGROUND OF THE DISCLOSURE

1. Field of the Invention

The present invention relates to novel synthetic peptides. More particularly, the invention relates to novel peptides which are useful as inhibitors of mammalian collagenase.

2. Background of the Prior Art

Collagenases are proteolytic enzymes which initiate the degradation of collagen in vertebrates. In addition to their normal function in the metabolism of connective tissue and wound healing, these endoproteinases have been implicated in a number of pathological conditions such as joint destruction in rheumatoid arthritis, periodontal disease, corneal ulceration and tumor metastasis.

Of particular significance is the pathological condition caused by corneal ulceration. Corneal ulceration is caused by different agents. One such cause is alkali burning of the cornea. Although methods of treatment are known, treatment of this condition continues to be a major challenge in ophthalmology.

Many therapeutic techniques have been used in an attempt to prevent the sequellae from threatening the intergrity of the eye following a chemical injury. These include corticosteroids, heparin, collagenase inhibitors, contact lenses, fibronectin, conjunctival flaps, and corneal transplantation. Recent studies have advocated the use of sodium citrate and sodium ascorbate. Following an ocular alkali burn, a number of degradative processes occur which may result in a corneal ulcer. Several proteases, including collagenases, are released in the chemically injured cornea and account for the ulcerative process. Although the multitude of treatment modalities used in these injuries undoubtedly work by different mechanisms of action, successful management of ocular alkali burns requires the use of agents which reduce the impact of collagenase and other proteases upon the cornea.

Heretofore, the efficacy of inhibitors of collagenases for use in human corneal alkali burns is open to question. Compounds which have been tested experimentally in animals include acetylcysteine, cysteine, sodium and calcium EDTA, and penicillamine. Of these, acetylcysteine which is approved for use as a mucolytic agent, is the only collagenase inhibitor used clinically in the treatment of human alkali burns. Its efficacy has yet to be proven in a randomized clinical trail. Collagenase inhibition by the tetracycline family of antibiotics has been demonstrated in vitro and systemic tetracycline has recently been shown to inhibit alkali-induced corneal ulceration in rabbits. Thus, an adequate inhibitor or collagenase for the treatment of alkali-induced corneal ulceration has not yet been developed and is a desired goal in ophthalmology.

Another cause of corneal ulceration is infectious keratitis. Infectious keratitis is the most common and most serious of the ocular infections. The organism *Pseudomonas aeruginosa* (PA) is one of the leading causes of infectious keratitis. The mainstay of therapy for infectious keratitis has been antimicrobial agents, but often, even when adequate levels of antibiotics are delivered, keratitis can progress to corneal ulceration and perforation. Many organisms, such as PA, release destructive enzymes which contribute to the breakdown of the cornea. In addition to enzymes released by the organism, host-derived enzymes, such as corneal collagenase, are also involved in the pathogenesis of infectious keratitis. Again, a new treatment for this condition is clearly a major current need in opthalmology.

Another area where collagenase inhibitors may be clinically important is the control of tumor metastasis. Malignant tumor cells differ from other cancer cells in their ability to spread through the mammalian body. To do this these cells must destroy connective tissue by giving off proteolylic enzymes including collagenases. It is thus postulated that collagenase inhibitors may slow down or even stop metastasis by inhibiting these enzymes.

Collagenase inhibitors have clinical significance in the control of certain forms of dermatitis. It has been found that proteolylic enzymes, including collagenases, are involved in the destruction of skin tissue. Therefore, the administration of a collagenase inhibitor would retard and/or prevent these dermatological diseases by inhibiting these enzymes.

The mechanism of action of mammalian collagenases on the molecular level is fairly well understood. Tissue collagenases hydrolyze a specific peptide bond at a single cleavage site on each of the three collagen chains of triple helical collagen. This cleavage site is contained within the amino acid sequence Pro-Gln-Gly-Leu-(Ile)-Ala-Gly-Gln-Arg, with cleavage occurring between glycine 775 and leucine or isoleucine 776, in Types I, II and III collagen, the predominant collagen in skin, bone, tendon, dentin, fascia and cartilage. Type IV collagenase (gelatinase) degrades basement membrane (Type IV) collagen, which may be important in tumor metastasis. The collagenases are metallopeptidases which contain an essential zinc at the active site. The zinc is assumed to function by interactions with the scissile carbonyl of the substrate, thus facilitating hydrolysis of the peptide bond.

Compounds which coordinate to the zinc active site have the ability to inhibit the activity of the collagenase. Because of the clinical importance and the desirability of being able to control these enzymes' activity, there has been a widespread effort to design compounds which are capable of interacting with the enzyme binding site and preventing the enzymes' action. Consequently, there exists a number of synthetic peptides and chemically similar compounds which are claimed to have at least some effect in inhibiting the activity of mammalian collagenases. Many of these synthetic peptides are constructed so as to mimic the natural amino acid sequence flanking the collagenase cleavage site. For example, U.S. Pat. No. 4,511,504 describes a number of carboxyalkyl peptide derivatives said to have inhibitory activity. U.S. Pat. No. 4,263,293 relates to heterocyclic-containing amide compounds, U.S. Pat. No. 4,235,885 discloses mercaptoacyl amino acid derivatives, U.S. Pat. No. 4,327,111 teaches N-substituted mercaptoacyl propionamides, U.S. Pat. No. 4,382,081 describes a wide variety of mercapto amino acid derivatives, all of which appear to have some level of collagenase inhibitory activity. Similarly, U.S. Pat. No. 4,374,765 refers to the use of acyl derivatives of the peptide Gly-L-Cys-Gly-L-Gln-L-Glu-NH2. U.S. Pat. No. 4,367,233 refers to thioglycolic acid derivatives, and U.S. Pat. No. 4,361,574 teaches alkanoic acid derivatives which are useful collagenase inhibitors. U.S. Pat. No. 4,595,700 sets forth thiol-based inhibitors. European Patent Application No. 85870005.7 discloses thiopeptolide derivatives as inhibiting collagenase substrates.

Hydroxamic acid based collagenase inhibitors have also been reported in European Patent Application Nos. 87102771.0 and 86112386.7.

In U.S. Pat. Nos. 4,599,361 and 4,743,587, Dickens, et al. disclose hydroxamic acid based compounds of the formula:

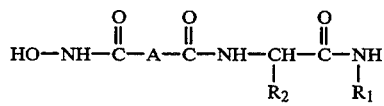

wherein $R_1$ is $C_1$–$C_6$ alkyl;

$R_2$ is $C_1$–$C_6$ alkyl, benzyl, benzyloxybenzyl, ($C_1$–$C_6$ alkoxy)benzyl; benzyloxy($C_1$–$C_6$ alkyl) or hydroxybenzyl;

A is either ($CHR_3$—$CHR_4$), or ($CR_3$=$CR_4$); where $R_3$ is hydrogen, $C_1$–$C_6$ alkyl, phenyl or phenyl ($C_1$–$C_6$ alkyl), $R_4$ is hydrogen, $C_1$–$C_6$ alkyl, phenyl ($C_1$–$C_6$ alkyl), cycloalkyl or cycloalkyl ($C_1$–$C_6$ alkyl).

These hydroxamic acid based compounds are alleged to be collagenase inhibitors.

Handa, et al. in European Patent Application No. 0 236 872 disclose compounds having the formula:

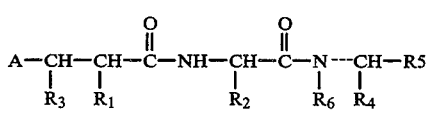

wherein

A is either HO—NH—CO or HCO—N(OH)—;

$R_1$ is $C_2$–$C_5$ alkyl;

$R_2$ is a natural amino acid having a functional group containing amino or carboxy with the proviso that $R_2$ is not hydrogen or methyl;

$R_3$ is hydrogen, amino, hydroxy, mercapto, $C_1$–$C_6$ alkyl, $C_1$–$C_6$ alkoxy, $C_1$–$C_6$ alkylthio, aryl ($C_1$–$C_6$ alkyl), amino ($C_1$–$C_6$ alkyl), hydroxy ($C_1$–$C_6$ alkyl), mercapto ($C_1$–$C_6$ alkyl) or carboxy ($C_1$–$C_6$ alkyl), wherein the amino, hydroxy, mercapto and carboxyl groups may be protected by an acylated amino group;

$R_4$ is hydrogen or methyl;

$R_5$ is hydrogen, $C_1$–$C_6$ methyl, $C_1$–$C_6$ alkoxy, $C_1$–$C_6$ alkyl, di($C_1$–$C_6$ alkoxy)carbonyl, arylmethoxycarbonyl, $C_1$–$C_6$ alkyl)aminocarbonyl or arylaminocarbonyl;

$R_6$ is hydrogen or methyl;

$R_2$ and $R_4$ may be taken together to form a $(CH_2)_n$ ring wherein n is 4 to 11; or $R_4$ and $R_5$ may be taken together to form a $(CH_2)_3$ ring.

The above compounds disclosed by Handa, et al. are alleged to inhibit collagenase.

In European Patent Application No. 0 262 053, Fournie-Zaluski, et al. disclose compounds of the formula:

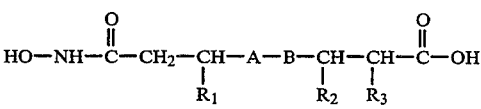

wherein $R_1$ is a saturated $C_1$–$C_{10}$ alkyl;

$R_2$ and $R_3$ are the same or are different and represent hydrogen or a $C_1$–$C_{10}$ saturated alkyl; and A-B is either

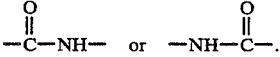

It is alleged that compounds of this formula inhibit collagenase.

Cartwright, et al. in European Patent Application No. 274 453 discloses compounds of the formula:

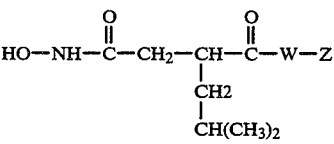

wherein W represents valine, lysine, norleucine or methionine; and

Z represents an amino radical or an alkylaminol in which the alkyl group contains 1 or 2 atoms of carbon and is substituted by a phenyl or a trifluorophenyl.

It is alleged that these compounds inhibit collagenase.

In U.S. Pat. Nos. 4,687,841 and 4,720,486, Spilburg, et al. disclose tripeptides of the formula:

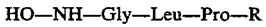

wherein R represent hydrogen, agaroses or an α-amino protecting group such as an alkanoyl, aroyl or cycloalkanoyl.

These compounds allegedly function either as collagen inhibitors or as affinity resins for the purification of vertebrate collagenase.

Wolanin, et al. in U.S. Pat. No. 4,771,038 disclose compounds having the formula:

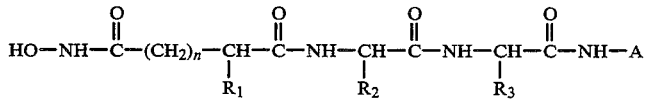

wherein $R_1$ is $C_2$–$C_7$ alkyl;

$R_2$ and $R_3$ may be the same or different and may be an amino acid residue chosen from the following: glycine, alanine, valine, leucine, isoleucine, phenylalanine, tyrosine, tryptophan, serine, threonine, cysteine, methionine, asparagine, glutamine, lysine, arginine, glutamic acid and aspartic acid, such that each amino residue, however, must not have an acidic terminus, but optionally may have an acidic side chain;

n is either 1 or 2; and

A is hydrogen or is —$CHR_4$—CO—$NH_2$, where $R_4$ is an amino acid residue.

Compounds of this formula are alleged to inhibit metalloproteases, particularly endopeptidases such as collagenase.

In addition to patents, the scientific literature also contains references to many collagenase inhibiting compounds. Clark, et al. (*Life Sciences* 37: 575–578 (1985)) refer to N[[5-chloro-2-benzothiazolyl)thiophenyl]acetyl]-L-cysteine, said to be a powerful mammalian collagenase inhibitor. Deleaisse, et al. (*Biochem Biophys. Res. Comm.* 133: 483–490, 1985) also refer to an inhibitor N-[3-N-(benzyloxy-carbonyl)-amino-1-(R)-carboxypropyl]-L-leucy-1-O-methyl-L-tyrosine-N-methylamide. Gray, et al. (*Biochem. Biophys. Res. Comm.* 101: 1251–1258, 1981) disclose a number of thiol-containing analogues of the collagen cleavage site. Additional thiol-containing peptides are disclosed by Gray, et al. in *J. Cell Biochem.*, 32: 71–77, 1986. Carboxyalkyl peptide analogues are described in Gray, et al. in *Federation Proc.* 44: 1431, 1985. Miller, et al. and Gray, et al. also disclose thiol-containing peptides in abstracts. [*Fed. Proc.* 45: 1859 (1986) and *FASEB J.* 2: A345 (1988), respectively]. Mookhtiar, et al. also discloses phosphonamidate inhibitors of collagenase. (see *Biochemistry*, 26, 1962 (1987)).

Despite the large number of compounds showing inhibitory properties, the therapeutically useful commercially available compounds are very few in number and are not altogether satisfactory in all respects for clinical use. Therefore, a continued need exists for an extremely potent and highly specific collagenase inhibitor which will have widespread therapeutic and commercial application. It has now been discovered that a small class of novel hydroxamic acid-containing tripeptides provides a level of collagenase inhibition not heretofore observed in the known inhibitory compounds.

BRIEF DESCRIPTION OF THE INVENTION

The present invention relates to compounds of the formula:

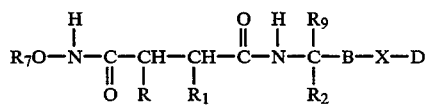

and pharmacutically acceptable salts thereof wherein

R and $R_1$ are independently hydrogen, lower alkyl, aryl or aryl lower alkyl;

$R_2$ is aryl lower alkyl or heterocyclic lower alkyl; said $R_2$ being unsubstituted or mono- or di-substituted with chloro, fluoro, bromo, nitro, carboxy, lower carbalkoxy, cyano, lower alkanoyl, trifluoromethyl, lower alkyl, hydroxy, lower alkoxy, formyl, amino, lower alkylamino, dilower alkylamino, mercapto, lower alkylthio or mercapto lower alkyl;

B is

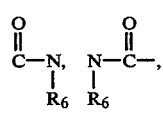

$CH_2S$, $CH_2SO$, $CH_2SO_2$,

$COCH_2$, $CH=CH$,

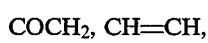

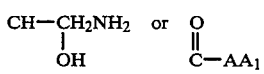

$AA_1$ is an amino acid residue;

X is a chemical bond, lower alkylene

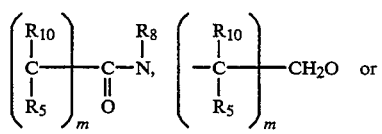

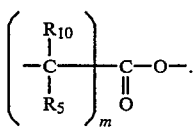

$R_9$ and $R_{10}$ are independently hydrogen, methyl or ethyl,

D, $R_5$, $R_6$, $R_7$, and $R_8$ are independently hydrogen or lower alkyl; and m is 1, 2, or 3, with the proviso that when B is

and X is a chemical bond or lower alkylene then $R_2$ is not unsubstituted benzyl or benzyl monosubstituted with hydroxy, or lower alkoxy and with the further proviso that when B is

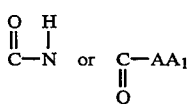

and X is

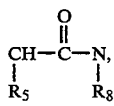

then $R_2$ is not unsubstituted indole or unsubstituted benzyl or benzyl monosubstituted with hydroxy or lower alkoxy.

The present invention also encompasses pharmaceutical compositions containing the aforementioned compounds as well as a method of treatment of collagenase related disorders which comprises administration to an animal suffering from said disorder of an inhibitory effective amount of the compound of Formula I.

DETAILED DESCRIPTION OF THE INVENTION

As defined herein, the term "lower alkyl," when used alone or in combination with other groups, represents an alkyl group containing one to six carbon atoms. These groups may be straight chain or branched. They include such groups as methyl, ethyl, propyl, isopropyl, butyl, isobutyl, sec-butyl, t-butyl, amyl, pentyl, hexyl and the like. It is preferred that the alkyl group contains 1-4 carbon atoms.

The term "aryl," when used alone or in combination with other groups, represents an aromatic moiety containing six to ten ring carbon atoms. This group includes phenyl, α-naphthyl, and β-naphthyl, and the like.

The term "aryl lower alkyl" refers to a group which contains a lower alkylene substituent to which is bonded an group. Examples include benzyl, α-naphthylenemethyl, β-napthylenemethyl, phenethyl, α and β-napthyleneethyl and the like. The preferred arylalkyl groups are benzyl and α- and β-naphthylenemethyl. The especially preferred aryl lower alkyl is α and β-naphthylene methyl.

The term "heterocyclic," when used alone or in combination, refers to a cyclic group containing at least one ring hetero atom selected from sulfur, oxygen or nitrogen. The heterocyclic substituent contemplated by the present invention includes heteroaromatics and saturated and partially saturated heterocyclics. These heterocyclic may be monocyclic, bicyclic or polycyclic and form fused rings. They may contain up to 18 ring atoms, up to 4 ring heteroatoms and up to a total of 17 ring carbon atoms and up to a total of 25 carbon atoms. The heterocyclics are also intended to include the benzoheterocyclics. Representative heterocyclics include thienyl, benzothienyl, naphthothienyl, furyl, pyranyl, pyrazolyl, pyrrolyl, imidazolyl, isoindolyl, indazolyl, isooxazolyl, indolyl, thiazolyl, piperazinyl, guinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazaolidinyl, pyrrolidinyl, furazanyl, N-methylindolyl, furfuryl, pyridyl, tetrahydrofuryl, pyridazinyl, pyrimidinyl, pyrazinyl, epoxy, aziridino, oxetanyl, azetidinyl, and the like. It is preferred that the heterocyclic moiety contain up to 10 ring atoms and up to a total of 4 ring heteroatoms. It is also preferred that the heterocyclic moiety be benzoheterocyclic. Further it is preferred that the heterocyclic moiety contain at least 1 ring nitrogen atom, and it is most preferred that the only ring heteroatom is nitrogen. It is also most preferred that the heterocyclic ring is an heteroaromatic in which the only heteroatom on the ring is nitrogen. It is especially preferred that the heterocyclic group contains only 1 ring nitrogen atom and be heteroaromatic. Examples of the preferred heterocycles include pyrrolyl, imidazolyl, pyrazolyl, tetrazolyl, pyridyl, pyrazinyl, pyrimidinyl, pyridazinyl, indolizinyl, isoindolyl, indolyl, indazolyl, purinyl, quinolizinyl, quinolyl, and isoquinolyl, and the like. The most preferred heterocyclic moiety is pyrrolyl, pyridyl, indolyl, isoquinolyl and quinolyl. The especially preferred heterocyclic ring is pyridyl, especially 2, 3- or 4-pyridyl, and indolyl, especially 3-indolyl.

The term heterocyclic lower alkyl refers to a group which contains a lower alkyl substituent to which is bonded a heterocyclic group. Examples include pyridylmethyl, indolylmethyl, pyridylethyl, indolylethyl, quinolylmethyl, and the like.

The term "alkanoyl" includes lower alkyl ketones and aldehydes. Examples include formyl, acetyl, propanoyl, butanoyl, and the like.

The term $AA_1$ refers to the naturally occurring amino acids. Preferably, these amino acids are α-amino acids. Most preferably, they are the twenty naturally occurring amino acids. These amino acids are recited below with the abbreviation for each used hereinafter in the specification and claims:

Ala—Alanine
Thr—Threonine
Gly—Glycine
Cys—Cysteine
His—Histidine
Met—Methionine
Leu—Leucine
Pro—Proline
Ile—Isoleucine
Lys—Lipine
Ser—Serine
Arg—Arginine
Asp—Aspartic Acid
Asn—Asparagine
Glu—Glutamic Acid
Gln—Glutamine
Phe—Phenylalanine
Tyr—Tyrosine
Trp—Tryptophan
Val—Valine These are the most preferred amino acids. Other amino acids contemplated by the present invention include napthylalanine (Nal), hydroxylysine (Hyl), hydroxyproline (Hyp), ethylglycine (EtGly), amino adipic acid (Aad), 2-aminobutyric acid (Abu), norvaline (Nva), norleucine (Nle), ornithene (Orn), sarcosine (Sar), N-methylglycine(MeGly), N-methylisoleucine (MeIle), N-methylvaline (MeVal) and dopamine (DOPA).

The most preferred $AA_1$ is glycine, alanine, valine, leucine, isoleucine, proline and N-methyl alanine. The especially preferred amino acid is alanine.

The alkyl groups, aralkyl groups, aryl groups, the heterocyclic groups and the heterocyclic alkyl groups as defined herein may be unsubstituted or substituted with electron donating or electron withdrawing groups. The terms "electron withdrawing" and "electron donating" refer to the ability of a substituent to withdraw or donate electrons relative to that of hydrogen if the hydrogen atom occupied the same position in the molecule. These terms are well understood by one skilled in the art and are discussed in *Advanced Organic Chemistry*, by J. March, John Wiley and Sons, New York, N.Y. pp. 16-18 (1985), and the discussion therein is incorporated herein by reference. Electron withdrawing groups include halo, including bromo, fluoro, chloro and iodo; nitro; carboxy; lower carbalkoxy; cyano; lower alkanoyl; mono, di-, tri-halo (lower) alkyl, e.g., trifluoromethyl; carboxyamido; formyl; sulfonyl; sulfinyl; ammonium; mono-, di-, tri- and tetra lower alkylammonium; heterocyclic; aryl, and the like. Electron donating groups include such groups as hydroxy; lower alkoxy; lower alkyl; amino; lower alkyl amino; di-(lower alkyl amino); aryloxy; mercapto; lower alkylthio; mercapto lower alkyl; lower alkyldithio and the like. The preferred substituents are lower alkyl, chloro, bromo, fluoro, lower alkoxy, lower alkylamino, diloweralkylamino, nitro, sulfonyl, mercapto, lower alkylthio, lower alkanoyl, and trifluoromethyl.

The preferred values of $R_7$ are hydrogen and alkyl containing 1-4 carbon atoms. The especially preferred $R_7$ is methyl and hydrogen. The most preferred is hydrogen.

It is preferred that R is hydrogen or methyl. The preferred value of $R_1$ is a butyl group, i.e., isobutyl, n-butyl, t-butyl or sec-butyl. The most preferred value of $R_1$ are sec-butyl and especially t-butyl.

As indicated hereinabove, $R_2$ may be arylalkyl or heterocyclicalkyl.

A preferred arylalkyl is dopa or 3,-4-dimethoxybenzyl.

Another preferred aryl alkyl is a napthylalkylene moiety of the formula:

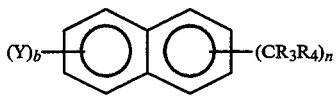

wherein $R_3$, and $R_4$ are hydrogen or lower alkyl and n is 1 or 2, Y is hydrogen, halo, nitro, carboxy, lower carbalkoxy, cyano, lower alkanoyl, trifluoromethyl, lower alkyl, hydroxy, lower alkoxy, formyl, amino, lower alkyl amino, dilower alkyl amino, mercapto, lower alkyl thio or mercapto lower alkyl, and b is 1 or 2. The preferred Y is H or $CH_3$. It is preferred that b is 1. The most preferred $R_3$ and $R_4$ are hydrogen. Moreover it is preferred that n is 1.

The most preferred napthylalkylene moiety is a 2-naphthylalkylene moiety of the formula:

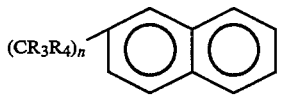

wherein $R_3$, $R_4$ and n are as defined hereinabove. Moreover, the most preferred value of napthylalkylene for $R_2$ is 2-naphthylmethylene.

As defined herein, $R_2$ can also be a heterocyclic lower alkyl moiety, i.e., $(CR_3R_4)_n$-heterocyclic, wherein, $R_3$, $R_4$, n and heterocyclic are as defined hereinabove. The preferred heterocyclic groups are described hereinabove. It is preferred that the heterocyclic group contains a nitrogen ring atom. Furthermore, the preferred heterocyclic groups are heteroaromatic. Finally, the most preferred heterocyclic groups are heteroaromatic and contain a nitrogen ring atom. Examples of the most preferred heterocyclic are pyrrolyl, pyridyl, indolyl, isoquinolyl, quinolyl and the like.

Especially preferred $R_2$ have the formula:

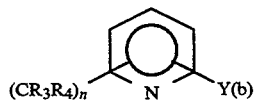

or

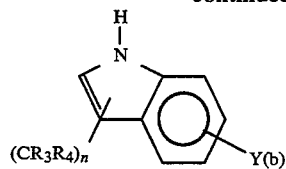

wherein $R_3$, $R_4$, Y, b and n are as defined hereinabove. The substituent $(CR_3R_4)_n$ can be substituted on the carbon ring atoms in the heteroaryl or can replace the hydrogen on the NH ring atom. It is preferred that the $(CR_3R_4)_n$ groups be substituted on the 2-, 3-, or 4-position of the pyridyl and the 2-, or especially the 3-position of the indolyl. It is preferred that n is 1 and it is also preferred that $R_3$ and $R_4$ are hydrogen.

It is preferred that Y is hydrogen, lower alkyl or lower alkoxy. Furthermore, it is preferred that b is 1.

The preferred value of m is 1.

The preferred value of $R_9$ is methyl and especially hydrogen. Similarly, the preferred value of $R_{10}$ is methyl, and especially hydrogen.

The preferred value of D is methyl, ethyl and especially hydrogen.

Further, the preferred value of X-D is

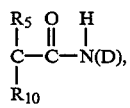

wherein $R_{10}$ is methyl or hydrogen and D is methyl, ethyl or hydrogen. The preferred X-D is

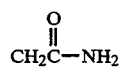

All combinations and permutations on the various variables described hereinabove are contemplated by the present invention.

It is to be noted that when B is other than

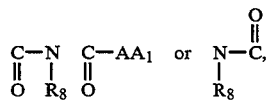

then the B linkage does not contain an amide linkage. Under these circumstances, B is a pseudopeptide ($\psi$). If a peptide is written as $AA_2\psi[B]AA_3$ where $AA_2$ and $AA_3$ are amino acids, this means that the amide linkage between $AA_2$ and $AA_3$ is replaced by B. For example, $Gly\psi(CH_2S)Ala$, means that alanine and glycine are linked by a $CH_2S$ group.

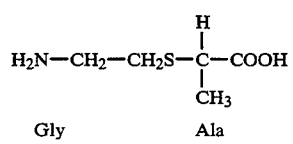

The compounds of the present invention are prepared by art recognized procedures. The starting materials of the reagents employed in the reactions hereinbelow maybe commercially available or may be prepared in accordance with standard techniques. A thorough discussion of the method of preparation is found in U.S. Pat. No. 4,599,361, the teachings of which are incorporated herein by reference.

More specifically, the compounds of the present invention can be prepared by reacting an acylating derivative of the hydroxamic acid (e.g., acid lower alkyl ester and the like) of Formula II

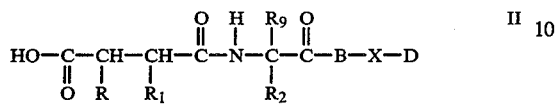

wherein R, $R_1$, $R_2$, $R_9$ $AA_1$, B, D and X are as defined hereinabove, with O-benzylhydroxylamine followed by hydrogenation. Alternatively, the hydroxamic acid can be prepared by coupling the acid directly with hydroxylamine using a coupling agent such as ethyl chloroformate. If desired, the products of Formula I may be separated into the individual isomers by chromatography.

The dipeptide of Formula II may be prepared by any of the wide range of known methods. For example, a protected carboxylic acid derivative, of Formula III can be reacted with a peptide of Formula IV under amide forming conditions, as shown below.

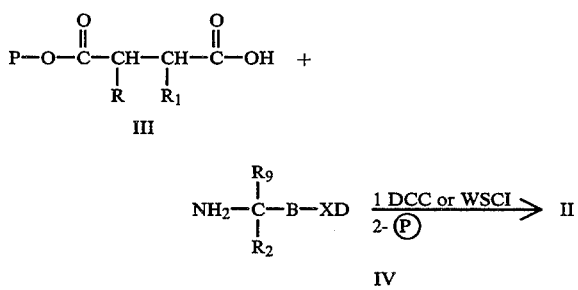

wherein R, $R_1$, $R_2$, B and X are as defined hereinabove, and P is a carboxylic acid protecting group, such as lower alkyl, e.g., t-butyl, which can easily be removed after the coupling shown hereinabove takes place. Among the more commonly used techniques are coupling using N,N'dicyclohexylcarbodiimide (DCC) or water soluble carbonyl diimide (WSCI) or the solid phase Merrifield synthesis, in which a protected amino acid is bound to a resin particle as an ester bond. Amino acids having functional groups such as tyrosine are generally protected with an easily removed blocking group, which are well known to the skilled artisan. Each of these techniques is equally suitable for the present purposes. The compounds so produced may be purified by chromatography, electrophoresis, or any other suitable means.

The corresponding protected carboxylic acid of Formula III, in which R is hydrogen, such as monosubstituted succinic acid lower alkyl ester, can be prepared by reacting diethyl succinate and an aldehyde of the formula $R_{11}CHO$ in the presence of a strong base, such as alkali t-butoxide, wherein $R_{11}$ is a homolog of $R_1$ containing one less carbon atom (i.e. $R_1$ is $R_{11}$—$CH_2$). The product thereof is hydrogenated. The resulting monoester is esterfied, such as by reacting isobutylene in the presence of an acid ($H^{30}$) and the product thereof is hydrolyzed in the presence of a base, e.g. NaOH. This procedure is described in U.S. Pat. No. 4,771,038, the discussion of which is incorporated herein by reference.

Alternatively when R is alkyl, hydrogen, aryl or aryl, lower alkyl, the compound of III is prepared by reacting a protected oxalic acid of Formula V.

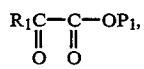

wherein $P_1$ is a protecting group such as benzyl with a phosphorous ylide-type compound, such as triethylphosphorous propionate, in the presence of a strong base (e.g., sodium hydride) under Wittig-Horner reaction conditions. An ylide-type compound can be prepared from a trialkoxy phosphorous such as (EtO)$_3$P and an α-bromo carboxylic acid ester, e.g.,

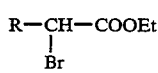

under Arbuzov reaction conditions.

The product is then hydrogenated to form the compound of Formula III.

The compound of Formula IV can also be prepared by art recognized techniques. For example, when B is

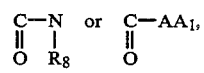

in which $R_8$ and $AA_1$ are as defined hereinabove, the compound of Formula IV can be prepared by reacting a protected amino acid acylating derivative of Formula VI with an amine of Formula VII as follows:

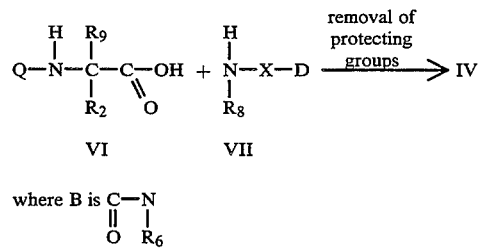

under amide forming conditions. In this scheme, Q is an amino protection group, such as t-boc, and B is

and X and $D_1$, $R_2$ and $R_6$ are as defined hereinabove. If D contains a carboxy group or a carboxy derivative which is also reactive under these reaction conditions, then these groups should be protected before the coupling takes place.

When B is

the reaction is very similar

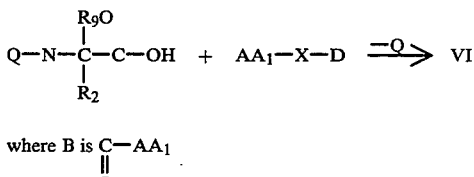

where B is C—AA$_1$
           ‖
           O

In the case when B is CH$_2$S, an exemplary procedure for making the product of IV is as follows:

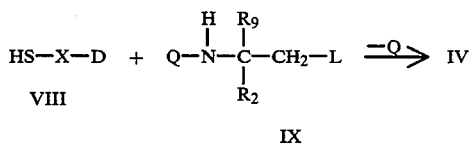

where B is CH$_2$S.

In this scheme, R$_2$, X, Q and D are as defined hereinabove and L is a good leaving group such as tosylate, halide and the like. In this reaction, the thiol of Formula VIII is reacted with a protected amino group having a good leaving group under nucleophilic substitution reaction conditions. Removal of the protecting group generates the product IV, wherein B is CH$_2$S.

The compound of Formula IX can be generated by the following exemplary reaction scheme:

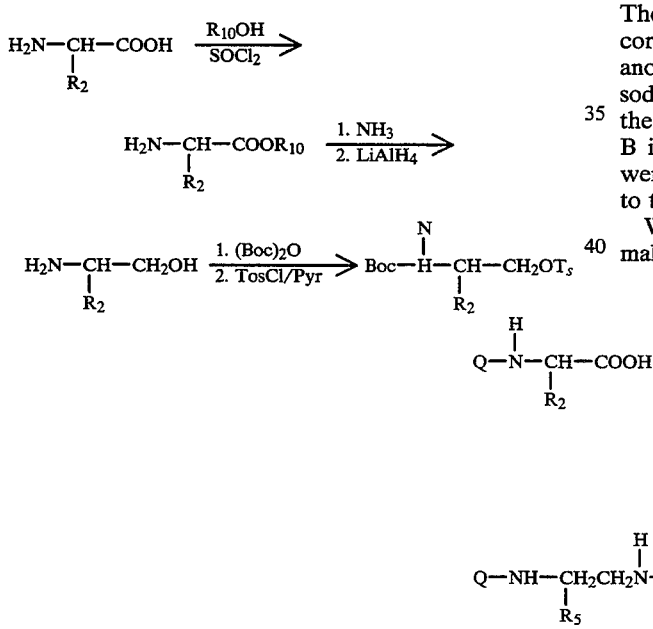

In this scheme B is CH$_2$S, R$_{10}$ is lower alkyl, Boc is butyloxycarbonyl, Q is an amino protecting group and OT$_S$ is tosylate, and L is a good leaving group. The amino acid of Formula X is esterified under esterification conditions and the resulting ester is reduced with a reducing agent, such as LiAlH$_4$. After protecting the amino group, a tosyl halide is reacted with the alcohol is base, such as pyridine to form the corresponding tosylate.

An exemplary scheme for forming the compound of Formula VIII is as follows:

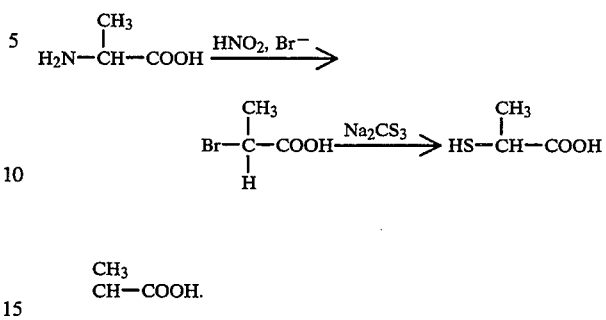

In this example, X—D is CH—COOH. The compound of Formula X is halogenated by, for example, reacting it with nitric acid and a bromide salt (e.g. NaBr), with retention of configuration. Under mercapto forming conditions, the halide is reacted with a salt of a mercapto, such as CS$_3$=, to form the corresponding thiol, with inversion of configuration.

The sulfoxides, i.e., compounds when B is CH$_2$SO and the sulfones, i.e., compounds wherein B is and CH$_2$SO$_2$ can be prepared from the corresponding thiols. Thus, for example, 1 mole of the compounds of Formula IV, wherein B is CH$_2$S or SCH$_2$ can be reacted with one mole of oxidizing agents, such as 30% H$_2$O$_2$, NaIO$_4$, t-BuO-Cl, acyl nitrite, sodium perborates, peracids and the like to form the corresponding sulfoxides. The sulfoxides in turn can be further oxidized to the corresponding sulfones by reacting the sulfoxide with another mole of oxidizing agent, such as H$_2$O$_2$, KMnO$_4$, sodium perborate, potassium hydrogen persulfate, and the like, to form the compound of Formula IV wherein B is CH$_2$SO$_2$ or SO$_2$CH$_2$. If excess oxidizing agents were present, then the sulfide can be directly converted to the sulfone without isolation of the sulfoxides.

When B is CH$_2$NH, an exemplary procedure for making the product of IV is as follows

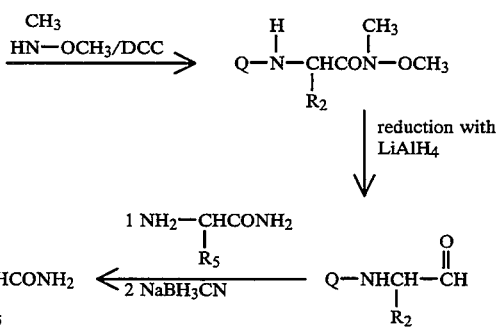

wherein Q, R$_2$, R$_5$ are as defined hereinabove. In the exemplary scheme, R$_9$ is hydrogen.

A protected amino acid is reacted with N, O-dimethylhydroxylamine in the presence of DCC or WSCI under amide forming conditions to form the corresponding hydroxamate. Reduction of the hydroxamate with a reducing agent such as LiAlH4 forms the corresponding aldehyde. The aldehyde is reacted with an amino acid derivative, such as an amide to form the Schiff base which is then reduced with a reducing agent, NaBH$_3$CN, under Castro NaBH$_3$CN reducing conditions to form the corresponding compound of Formula IV wherein B is CH$_2$NH.

The ketomethylene compounds of the present invention

can be prepared by techniques known to one skilled in the art. These techniques are described by Jennings-White, et al. *Tetrahderon Letters,* 73, 2533–2534 (1982), Almquist, et al. in *J. Med. Chem.,* 23, 1392–1398 (1980), Almquist, et al. in *J. Med. Chem.,* 25, 1292–1299 (1982) and Holladay, et al. in *Tetrahedron Letters,* 24, 4401–4404 (1983). These papers describe various methods for preparing ketomethylene linkages, and the procedures therein for can be used to make the ketomethylene linkages in compounds of the present invention. These references are therefore incorporated herein by reference as if they were set forth fully hereinbelow.

If the substituents on the starting compounds or intermediates themselves are reactive, then the substituents can themselves be protected according to techniques known to one skilled in the art. A variety of protecting groups known in the art may be employed. Examples of many of these possible groups may be found in "Protective Groups in Organic Synthesis" by W. Green, John Wiley and Son, 1981.

The compounds of the invention contain at least one asymmetric carbon atom, which is designated in the formula below by an asterisk

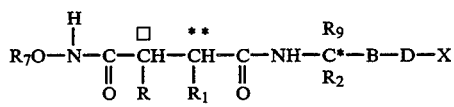

Furthermore, the groups CH(R) and CH(R1) and

are pesudoasymmetric groups, [(**) and (☐)] each of which can contain additional asymmetric carbon when R or $R_1$ is other than hydrogen and $R_{10}$ is other than $R_5$. Each of the asymmetric carbons gives rise to chiral centers, and each of the chiral centers can exist in either the R or S forms. Each of the various stereoisomers, including the enantiomers and diastereoisomers, are contemplated by the present invention. The pure stereoisomers as well as a mixture thereof are contemplated by the present invention. However, it is preferred that the configuration at the asterisked carbon be S. It is also preferred that the configuration around the double asterisked carbons also be in the S form. In the more preferred form, the configuration around each of the indicated chiral centers is in the S form.

Moreover, these stereoisomers can be separated by art recognized techniques known in the art. For example, the amino acids which are commercially available and are substantially optically pure, are used as starting materials onto which the peptide builds. Therefore, the various stereoisomeric products formed by the reaction described hereinabove would be diastereomeric pairs, which can be resolved by standard chromatographic techniques.

The present new compound form salts with acids when a basic amino function is present and salts with bases when an acid function, i.e., carboxy, is present. All such salts may be useful in the isolation and/or purification of the new products. Of particular value are the pharmaceutically acceptable salts with both acids and bases. Suitable acids include, for example, hydrochloric, sulfuric, nitric, benzenesulfuric, toluenesolfonic, acetic, malic, tartaric and the like which are pharmacetucially acceptable. Basic salts for pharmaceutical use are the Na, K, Ca and Mg salts.

In those peptides in which Arg is added, acid addition salts may also be prepared, particularly acetate or hydrochloride salts. Although for obvious reasons, pharmaceutically acceptable salts are preferred, the invention is not limited to them since non-pharmaceutically acceptable salts may prove useful in isolating the compounds of the invention.

The compounds of the present invention can be administered to the host in a variety of forms adapted to the chosen route of administration, i.e., orally, intraveneously, intramuscularly or subcutaneous, topically or inhalation routes. Topical application is extremely important when treating dermatological diseases.

The compounds of the present invention can be employed in the treatment of any disease in which collagenase has been implicated as a central factor; such as for example, corneal ulceration, osteophorosis, peridontitis, Paget's disease, gingivitis, tumor invasion, dystrophic epidermolysis bullosa, systemic ulceration, epidermal ulceration, gastric ulceration, and the like.

The pharmaceutical compositions according to the invention may, for example, take the form of ointments, gels, pastes, creams, sprays (including aerosols), lotions, suspensions, solutions and emulsions of the active ingredient in aqueous or non-aqueous dilutents, syrups, granulates or powders.

The pharmaceutical compositions which are ointments, pastes, creams and gels can, for example, contain the usual diluents, e.g. animal and vegetable fats, waves, parrafins, starch, tragacanth, cellulose derivatives, polyethylene glycols, silicones, bentonites, silic acid, talc and zinc oxide or mixtures of those substances.

The pharmaceutical compositions which are powders and sprays, can, for example, contain the usual diluents, e.g. lactose, talc, silic acid, aluminum hydroxide, calcium silicate, and polyamide powder or mixtures of these substances. Aerosol sprays can, for example, contain the usual propellants, e.g. chlorofluorohydrocarbons.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excepients and used in the form of ingestible tablets, buccal tablets, troches, capsules, elixirs, suspensions, syrups, wafers, and the like. Such compositions and preparations should contain at least 0.1% of active compound. For parental administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages, substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with those other therapeutic agents.

When given orally, the therapeutic doses of the compounds of the present invention are generally effective, even in the nanomolar range, and these compounds are effective in micromolar quantities in the range of from about 10 to about 500 mg/kg of body weight of treated mammal. When given parenterally, the compounds are administered generally in dosages of, for example, 0.01 mg/kg to about 200 mg/kg, also depending upon the host and effect desired. The preferred dosage ranges from 0.5 to 10 mg/kg of body weight of treated mammal.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples are given to illustrate the present invention. These examples are provided solely for the illustration purposes. Therefore, the invention should not be limited thereto.

EXAMPLE 1

Preparation of Hydroxamic Acid Based Collagenase Inhibitors: Synthesis of $HONHCOCH_2CH_2(CH_2CH(CH_3)_2)CO—NAL—ALA—NH$ A. 3-Ethoxycarbonyl-3-(2-methylpropyl)propanoic acid Potassium t-butoxide, 24.7 g (0.35M), was dissolved in 200 ml of refluxing t-butanol. A mixture of isobutyraldehyde, 18.2 ml (0.20M) and diethyl succinate 41.55 ml (0.25M) was added to the t-butanol solution over 30 min. The reaction mixture was stirred under reflux, for 2 h. The solvent was removed from the reaction mixture by evaporation under reduced pressure and acidified with 2N HCl. The product was extracted with ethyl ether, Et2O (3×200 ml). The ether solution was washed with water (3×200 ml); and the product was extracted with 10% Na2CO3 (4×200 ml). The solution was acidified with conc. HCl solution and the product was isolated by extraction with Et2O (4×150 ml). The ether layer was washed with water, dried over sodium sulfate, and evaporated. The remaining oil was dissolved in ethanol (300 ml) and hydrogenated in the presence of 10% palladium on charcoal (3.0 g). The resultant mixture was filtered through Celite and the solvent was evaporated to yield 38.04 g 2-carboethoxycarbonyl-4-methyl pentanoic acid as a mixture of isomers in the form of an oil. The isolated monoethyl ester was further purified on silica gel by flash chromatography using as eluent mixture ethyl acetate:hexane:acetic acid (1:10:0.05, v/v).

NMR: (300 MHz, CDCl3): δ (ppm) 0.90 (6H, q, (CH3)2CH); 1.20–1.38 (4H, m, CH3 ester+(CH3)2C$\underline{H}$;

1.56(2H, m, C̲H̲2—CH); 2.45 and 2.72 (2H, dd and q, HOOC—C̲H̲2); 2.84 (1H, m, CH2—C̲H̲—CO); 4.14 (2H, q, C̲H̲2 ester).

B. 2-Carbo-t-butoxycarbonyl-4-methylpentanoic acid

To a chilled (−70°) solution of 3-(ethoxycarbonyl)-3-(2-methylpropyl)propanoc acid (23.0 g) in 200 ml of methylene chloride was added isobutylene, 200 ml and conc. sulfuric acid (4 ml). The reaction mixture was stirred in a glass medium pressure reaction vessel for 4 days at RT. Then the solution was cooled to −70° C., opened, and saturated NaHCO3 solution was added (80 ml). The remaining solvents were evaporated and product was extracted with ethyl ether (3×200 ml). The ether solution was washed with H2O, dried over Na2SO4, and evaporated to yield the diester (29.48 g) as an oil. Diester (29.48 g) was hydrolyzed with 2N NaOH (40.5 ml) in 300 ml 50% aqueous ethanol for 12 h at RT. Then ethanol was evaporated and remaining oil was diluted with water and extracted with ethyl ether (3×200 ml). The aqueous solution was acidified with 2N HCl to pH=2 and product was taken into Et2O and gave after evaporation of solvent, 15.83 g of product as an oil. The obtained monoester was purified on silica gel by flash chromatography using as eluent ethyl acetate:-hexane:acetic acid (1:9:0.1, v/v).

NMR: (300 MHz, CDCl3): δ (ppm) 0.90 (6H, q, (CH3)2—CH); 1.27 (1H, m, (CH3)2C̲H̲); 1.41 (9H, s, (C̲H̲3)3—C); 1.60 (2H, m, (CH3)2CH—C̲H̲2); 2.34 and 2.55 (1H and 1H; dd and q, CO—CH2—C̲H̲); 2.82 (1H, m, C̲H̲—COOH).

C. Preparation of HO—NH—CO—CH2—CH(CH2CH(CH3)2)—CO—Nal—Ala—NH2

To the chilled (0° C.) solution of t-butyl ester (0.512 g) and L-naphtylalanyl-L-alanine amide hydrochloride (0.808 g) in dimethylformamide was added triethylamine (0.42 ml) and then slowly by parts N-ethyl-N'-(3-dimethyl amino propyl) carbodiimide (0.479 g) over 15 min. The reaction mixture was stirred for 2 h at 0° C. and overnight at RT. The next day, ethyl acetate (100 ml) was added and the solution was washed three times with 50 ml portions of 1N HCl, NaHCO3(sat), brine, and dried over magnesium sulfate. A white solid material (0.44 g) obtained after evaporation of solvent, was treated with 6N HCl/dioxane at RT for 60 min to remove the t-butyl ester group. Evaporation of dioxane and precipitation with ethyl ether gave a white solid product (0.320 g) which was then coupled to 0-benzyl hydroxylamine again using the EDC procedure with triethylamine as listed above. Catalytic hydrogenation (10% Pd/C, MeOH, 4 h) was used to remove the benzyl protecting group, giving the hydroxamic acid product as a mixture of two diastereoisomers. The isomers were isolated using reversed phase chromatography on a C-18 Dynamax column using an isocratic TFA/AcCN elution mixture. The final products were lyophilized and characterized as specified below.

NMR (ISOMER I): (300 MHz, DMSO-d6): δ (ppm) 0.64 and 0.73 (6H, 2xd, (C̲H̲3)2CH); 0.90 (3H, m, (CH3)2—CH—CH2 and (C̲H̲3)2—CH—CH2); 1.22 (3H, d, CH3—C̲H̲); 2.64 and 3.00 (1H, and 1H, m, CH2—Cl0H7); 1.84-1.96 (3H, m, CO—CH2—CH); 4.20 (1H, m, C̲H̲—CH2Cl0H7); 4.56 (1H, m, CH—CH3); 6.98 and 7.21 (1H and 1H, s, CO—NH2); 7.40-7.90 (8H, m, Cl0H7 and CH2—CH—CO—NH̲—); 8.18 (1H, d, CO—NH̲—CH—CH3); 8.66 (1H̲, s, NH—OH); 10.32 (1H, s, NH—OH̲).

HPLC (ISOMER I): Rt=13.5 min, Hibar C18 (4.7×150 mm), gradient 30-60% B in 30 min, A: 0.05% aqueous TFA; B: 0.05% TFA in AcCN, 1 ml/min.

NMR (ISOMER II): (300 MHz DMSO-d6): δ (ppm) 0.24 (3H, d, (CH3)2CH); 0.38 (4H, m, (CH3)2CH and (CH3)2C̲H̲); 0.70 and 1.08 (1H and 1H, m, (CH3)2—CH—C̲H̲2); 1.34 (3H, d, CH3—CH); 1.92 and 2.02 (1H and 1H, m, CO—CH2—CH); 2.86 and 3.34 (1H and 1H, m, C̲H̲2—Cl0H7); 2.47 (1H, m, CH2—C̲H̲—CO); 4.23 (1H̲, m, CH2Cl0H7); 4.55 (1 H, m, CH—C̲H̲3); 7.02 and 7.15 (1H and 1H, s, CO—NH2); 7.44-7.78 (7H, m, Cl0H7); 8.00 (1H, d, CH2CO—N̲H̲—); 8.42 (1H, d, CO—N̲-H—CH—CH3); 8.68 (1H, s, N̲H̲—OH); 10.50 (1H, s, NH—OH̲).

HPLC (ISOMER II): Rt=15.9 min, Hibar C18 (4.7×150 mm), gradient 30-60% B in 30 min, A: 0.05% aqueous TFA; B: 0.05% TFA in AcCN, 1 ml/min.

EXAMPLE II

Preparation of HO—NH—CO—CH2—CH(CH2CH(CH3)2—CO—Nal—Pro—NH2

To a chilled (0° C.) solution of naphthylalanylalanine hydrochloride (0.50 g), t-butyl ester (0.3 g), N-hydroxybenzotriazole (0.22 g), and BOP (0.67 g) in DMF was added triethylamine (0.6 ml). The reaction mixture was stirred for 1 h at 0° C. and for 16 h at RT. Then the reaction mixture was diluted with AcOEt (100 ml), washed with 3×1N HCl, 3×NaHCO3(sat), brine, and dried over MgSO4. Crude product was purified by flash chromatography on silica gel using solvent system AcOEt:AcOH(100:1 v/v). After evaporation of the solvent, the major fraction gave 0.6 g of solid product. Removal of t-butyl ester from succinyldipeptide was carried out by 10N solution of HCl/dioxane. Evaporation of dioxane and precipitation with diethyl ether gave 0.52 g of product which was further coupled to O-benzylhydroxylamine using EDC method in the presence of Et3N as described in Example I. The resulting product was hydrogenated (10% Pd/C, MeOH 6 h) to remove benzyl protecting group. Hydroxamic acid was obtained as a mixture of two diastereoisomers. The isomers were isolated using preparative reversed phase chromatography as described in Example I. Final products were lyophilized and characterized as specified below:

Isomer I

HPLC: Rf=6.92 min, Vydac C18 (218TP54, 4.6×250 mm), gradient 30→60% B in 30 min, 1 ml/min. A: 0.05% aqueous TFA; B: 0.05% TFA in AcCN. FAB-MS: cal. 482; found MH+483, M+Na+505

Isomer II

HPLC: Rf=10.43 min, Vydac 98 (218TP54, 4.6×250 mm), gradient 30→60% B in 30 min, 1 ml/min. A: 0.05% aqueous TFA; B: 0.05% TFA in AcCN FAB-MS: calc., MW=482; found M+H+483; M+Na+503

EXAMPLE III

Preparation of HO—NH—CO—CH(CH3)—CH(CH2—CH(CH3)2)—CO—Nal—Aln—NH2

4-methyl-2-oxopentanoic acid benzyl ester (1)

To the cooled solution of 4-methyl-2-oxo-pentanoic acid (10 g), benzyl alcohol (9.56 g) and 4-methyl aminopyridine (0.93 g) in 50 ml of methylene chloride was added slowly N-ethyl-N'-(3-dimethylaminopropyl) carbodiimide over 30 min. The reaction mixture was stirred 1 h at 0° C. and overnight at RT. The next day, $CH_2Cl_2$ was evaporated, the oily residue was dissolved in 200 ml ethyl acetate and washed three times with one of the following: 1N HCl, 10% $Na_2CO_3$, brine, then dried over $MgSO_4$. The crude compound (19.19 g) after evaporation of AcOEt was purified by flash chromatography on silica gel using ethyl acetate/hexane mixture as eluent. After evaporation of the solvents, the major fraction gave 13.26 g of oily product.

NMR (300 MHz, $CDCl_3$)

δ (ppm): 0.96 (6H, d, $(CH_3)_2$—CH); 2.20 (1H, m, $(CH_3)_2C\underline{H}$); 2.74 (2H, d, $\underline{CH_2}$—CH); 5.28 (2H, s, $CH_2$—$C_6H_5$), 7.40 (5H, m, $C_6\underline{H_5}$).

2-(1'-Ethoxycarbonyl ethyl)-4-methylpentanoic acid (2)

Triethylphosphorus propionate (5.975 g, 25 mM) was added into suspension of sodium hydride (80% mineral oil suspension) 0.75 g in 100 ml of dry toluene at room temperature. The reaction mixture was heated up to 50°–60° C. until sodium hydride was dissolved. Then the reaction mixture was cooled to −70° C. and benzyl 4-methyl-2-oxopentanoate 5.0 g (38 mM) was added and the resulting mixture was allowed to warm up to room temperature and was stirred for an additional 1 h at RT. The toluene solution was washed with 10% citric acid 3 x, water (3 x), and dried over $MgSO_4$. The obtained oil (7.01 g) was hydrogenated in 300 ml of EtOH in the presence of 1 g of 10% palladium/carbon for 96 h. Then the catalyst was filtered and the solvent was removed under reduced pressure. The crude product (4.8 g) was purified by flash chromatography on silica gel using a mixture of AcOEt/hexane/AcOH (1:3:0.01 v/v) as an eluent. Major fraction (2.26 g) was obtained after evaporation of solvents.

NMR (300 MHz, $CDCl_3$)

δ (ppm): 0.86 (6H, m, $(CH_3)_2C$); 1.18 (3H and 1H, d and m, $CH_3$—CH and $(CH_3)_2C\underline{H}$); 1.23 (3H, t, $CH_3$ ester) 1.60 (2H, m, $\underline{CH_2}$—CH); 2.68 (1H+1H, m+m, $C\underline{H}$—CH); 4.12 (2$\underline{H}$, q, $CH_2$ ester). HO—NH—CO—CH($CH_3$)—CH($CH_2$—CH($CH_3$)$_2$)—CO—Nal—Ala—$NH_2$ To the cooled solution (0° C.) of monoethyl ester (1.08 g), naphthylalanylalanine amide hydrochloride (1.67 g) and (benzotriazolyloxy) tris-(dimethylamino)-phosphonium hexafluorophosphate (BOP) 2.21 g in 5 ml of DMF was added triethylamine (2.1 cm³). The reaction mixture was stirred for 2 h at 0 C. and overnight at RT. Then the reaction mixture was diluted with ethyl acetate (100 ml) and washed three times with the following: 1N HCl, $NaHCO_3$ (sat), brine, and dried over $MgSO_4$. A white solid material (0.65 g) obtained after evaporation of AcOEt and precipitation with hexane was saponified with 1 N NaOH in methanol/water solution. The resulting product (0.52 g) was coupled into O-benzyl hydroxylamine using EDC procedure with $Et_3N$ as described above for example I. Catalytic hydrogenation (100% Pd/carbon, MeOH, 4 h) was used to remove the benzyl protecting group, giving hydroxamic acid product as mixture of four isomers. The isomers were isolated using reversed phase chromatography on $C_8$-Dynamax column using an isocratic elution with AcCN:$H_2O$:TFA (39:61:0.1 v/v). Final products were lyophilized and characterized as specified below:

Isomer I

NMR (300 MHz in DMSO-$d_6$): δ (ppm): 0.18 (3H, s, $(CH_3)_2CH$—); 0.32 (4H, bs, $(CH_3)_2CH$— and $(CH_3)_2C\underline{H}$—); 0.64 and 1.12 (1H and 1H, m and m, $(CH_3)_2$—CH—$CH_2$); 0.90 (3H, d, $C\underline{H_3}$—CH); 1.26 (3H, d, $C\underline{H_3}$—CH—$CONH_2$); 2.06 (1H, m, $CH_3C\underline{H}$); 2.32 (1H, m, $(CH_3)_2CH$—$CH_2$—$C\underline{H}$); 2.92 and 3.24 (1H and 1H, m and m, $C\underline{H_2}$—$C_{10}H_7$); 4.26 (1H, m, $C\underline{H}$—$CH_2$—$C_{10}H_7$); 4.62 (1H, m, $CH_3$—$C\underline{H}$); 7.00 and 7.28 (1H and 1H, s and s, CO—$NH_2$); 7.46–7.84 (8H, m, $C_{10}H_7$ and NH—CH —$C\underline{H_2}$—$C_{10}H_7$); 8.36 (1H, d, $CH_3CH$—$N\underline{H}$); 8.66 (1H, 6s, NH—$O\underline{H}$); 10.38 (1H, s, $N\underline{H}$—OH).

HPLC: $R_f$=7.67 mm, Vydac $C_{18}$(218TP54, 4.6×250 mm), gradient 30→60% B in 30 min, 1 ml/min. A: 0.05% aqueous TFA; B: 0.05% TFA in AcCN FAB-MS: calc. 470; $M+H^+$=471; $M+Na^+$=493.

Isomer II

NMR (300 MHz in DMSO-$d_6$): δ (ppm): 0.64 (9H, m, $(CH_3)_2CH$ and $CH_3CH$); 0.92 (1H, m, $(CH_3)_2C\underline{H}$); 1.34 and 1.14 (1H and 1H, m and m, $(CH_3)_2$—CH—$CH_2$); 1.20 (3H, d, $CH_3$—CH—$CONH_2$); 2.18 (1H, m, $CH_3$—$C\underline{H}$); 2.40 (1H, m, $(CH_3)_2$—$C\underline{H}$); 2.96 and 3.22 (2H, m, $\underline{CH_2}$—$C_{10}H_7$); 4.20 (1H, m, $C\underline{H}$—$CH_2C_{10}H_7$); 4.66 (1H, m, $CH_3CH$—$CONH_2$); 6.96 and 7.22 (1H and 1H, s and s, $CON\underline{H_2}$); 7.42–7.80 (7H, m, $C_{10}H_7$); 7.96 (1H, d, NH—CH—CH $_2$—$C_{10}H_7$); 8.16 (1H, d, $CH_3$—CH—$N\underline{H}$); 8.66 (1H, bs, NH—$O\underline{H}$); 10.32 (1H, s, $N\underline{H}$—OH);

HPLC: $R_f$=7.89 min; Vydac $C_{18}$(218TP 54, 4.6×250 mm), gradient 30→60% B in 30 min, 1 ml/min. A: 0.05% aqueous TFA; B: 0.05% TFA in AcCN FAB-MS: calc. 470; found $M+H^+$=471; $M+Na^+$=493.

Isomer III

NMR: δ (ppm): 0.76 (9H, m, $(CH_3)_2CHCH_2$ and $CH_3$—CH); 1.04 (1H, m, $(CH_3)_2C\underline{H}$—$CH_2$); 1.24 (1H, m, $(CH_3)_2CH$—$CH_2$); 1.34 (4H, bd, $CH_3$—CH and $(CH_3)_2CHCH_2$); 2.08 (1H, m, $CH_3$—$C\underline{H}$); 2.40 (1H, m, $(CH_3)_2CHC\underline{H_2}C\underline{H}$); 2.86 and 3.18 (1H and 1H, m, $C\underline{H_2}$—$C_{10}H_7$); 4.24 (1H, m, $C\underline{H}$—$CH_2$—$C_{10}H_7$); 4.48 (1$\underline{H}$, m, $CH_3$—$C\underline{H}$); 7.10 (1H, s, $CON\underline{H_2}$); 7.40–7.80 (8H, m, $C_{10}H_7$ and $CONH_2$); 7.80 (1$\underline{H}$, d, $N\underline{H}$—CH—$CH_2$—$\underline{C_{10}}H_7$); 8.28 (1$\underline{H}$, d, NH—CH—$CH_3$); 8.66 (1H, s, NH—$O\underline{H}$); 10.56 (1H, s, $N\underline{H}$—OH).

HPLC: $R_f$=11.84, Vydac $C_{18}$ (218TP54, 4.6×250 mm), gradient 30→60% B in 30 min, 1 ml/min. A: 0.05% aqueous TFA; B: 0.05% TFA in AcCN FAB-MS: calc. 470; found $M+H^+$=471; $M+Na^+$=493.

Isomer IV

NMR: δ (ppm): 0.08 (4H, m, $(CH_3)_2CH$ and $(CH_3)_2CH$—); 0.40 (2H, d, $(CH_3)_2C\underline{H}$); 0.82 and 1.02 (1H and 1H, m, $(CH_3)_2C\underline{H}$—$CH_2$); 0.96 (3H, d, $CH_3$—CH); 1.42 (3H, d, $CH_3$—$C\underline{H}$—$CONH_2$); 2.08 (1$\underline{H}$, m, $CH_3$—$C\underline{H}$); 2.26 (1$\underline{H}$, m, $(CH_3)_2CH$—CH$_2$—$C\underline{H}$); 2.80 (1$\underline{H}$, m, $CH_2$—$C_{10}H_7$); 4.28 (1H, m, $C\underline{H}$—$CH_2$—$C_{10}H_7$); 4.56 (1$\underline{H}$, m, $CH_3$—$C\underline{H}$); 7.22 (1H, s, $CON\underline{H_2}$); 7.38–7.82 (9H, m, $C_{10}H_7$ and NH—CH—$C\underline{H_2}$—$C_{10}H_7$ and $CONH_2$); 8.38 (1H, d, $CH_3$—CH—$N\underline{H}$); 8.78 (1H, bs, $N\underline{H}$—$O\underline{H}$); 10.62 (1H, s, NH—$O\underline{H}$).

HPLC: $R_f$=12.82 min, Vydac $C_{18}$(218TP54, 4.6×250 mm), gradient 30→60% B in 30 min, 1 ml/min. A: 0.05% aqueous TFA; B: 0.05% TFA in AcCN.

FAB-MS: calc. 470; found $M+H^+$=471, $M+Na^+$=493.

EXAMPLE IV

Preparation of
HO—NH—CO—CH$_2$—CH(CH$_2$CH(CH$_3$)$_2$)—CONalψ[CH$_2$S]—Ala—NH$_2$ A. H—Nal—CH$_2$OH L-naphthylalanine-methyl ester hydrochloride (4.0 g; 15 mmol) was suspended in CHCl$_3$(60 ml) and an excess of solution of NH$_3$ in CHCl$_3$ was carefully added. The mixture was stirred at room temperature for 15 minutes, then the NH$_4$Cl formed was filtered. The white oil residue was dissolved in anhydrous ether (100 ml) and added, dropwise, to a suspension of LiAlH$_4$ (0.76 g; 20 mmol) in ether (60 ml). After complete addition, the reaction was stirred at room temperature for 3 h. Water was added and the pH was adjusted to 10 with 2H NaOH, then the product was extracted with ether (60 ml). The organic layer was washed with water, dried over Na$_2$SO$_4$, filtered and evaporated. The product was collected as a yellowish solid (2.76 g; 91% yield): mp 98°–100° C.

B. Boc—Nal—CH$_2$OH

L-naphthylalaninol (2.72 g; 13.5 mmol) was dissolved in teributanol (60 ml) and di-t-butyl pyrocarbonate (3.16 g; 14.5 mmol) was added. The reaction was stirred at room temperature for 3 h, then the solvent was removed in vacuo. A white solid was crystallized from AcOEt/hexane (3.47 g; 92% yield): mp 131°–132° C.

C. Boc—Nal—CH$_2$OTs

N-t-butyloxycarbonylnaphthylalaninol (3.71 g; 12.3 mmol) was dissolved in pyridine (15 ml) and the solution was cooled to −30° C. Tosyl chloride (2.36 g; 12.4 mmol) was added and the mixture was stirred to clearness at −30° C. and then put into the refrigerator overnight. Pyridine was removed in vacuo and the product was extracted with ether (4×30 ml). The organic layer was washed with 1N HCl (2×30 ml), H$_2$O (1×30 ml), NaHCO$_3$ 5% (2×30 ml) and saturated NaCl (1×30 ml), then dried over Na$_2$SO$_4$, filtered and stripped to leave an oily residue which was crystallized from AcOEt/hexane (4.6 g; 82% yield).

D. D-2-Br-propionic acid

D-Ala (4.45 g; 50 mmol) and KBr (24 g; 200 mmol) were dissolved in 2.5N H$_2$SO$_4$ (150 ml) and the solution was cooled to −5° C. NaNO$_2$ (7.6 g; 110 mmol) dissolved in water (30 ml) was added, dropwise, over a period of 1 h and after this time the reaction was stirred at 0° C. for 1 h and at room temperature for 5 h. The product was extracted with ether (3×50 ml) and the organic solution was washed with H$_2$O and saturated NaCl, then dried over Na$_2$SO$_4$, filtered and stripped to a yellowish oil. The oil was distilled in vacuo, yielding a colorless oily product (3.73 g; 54% yield).

E. L-2-thio-propionic acid

The product of D (5.87 g; 38 mmol) was added, dropwise, to a solution of sodium thiocarbonate in water (25 ml; 33% v/v) and cooled to 0° C. for 2 h and at room temperature for 5 days. After this time, the solution was carefully acidified to pH 2 with 10N H$_2$SO$_4$ and the product was extracted with ether (4×50 ml). The organic layer was washed with H$_2$O, dried over Na$_2$SO$_4$, filtered and evaporated in vacuo. The oily residue was distilled in vacuo, yielding a colorless oil (3.0 g; 76% yield).

F. Boc—Nalψ[CH$_2$S]Ala—OH

In a 3-neck round bottom flask were placed absolute ethanol (30 ml) and sodium (0.23 g; 10 mmol). Nitrogen was bubbled into the flask and then 10 (0.53 g; 5 mmol) in ethanol (5 ml) was added. The solvent was immediately removed in vacuo. The solution of N-t-butylcarbonyl naphthylalanine tosylate (2.46 g; 5.5 mmol) in DMSO (10 ml) was added to the flask. The reaction was stirred at room temperature for 6 h under a nitrogen blanket. NaHCO$_3$ 5% (150 ml) was added and the excess of Boc—Nal—CH$_2$OTs was extracted with AcOEt. The aqueous layer was acidified to pH 2 with 2N HCl, then extracted with AcOEt 94×50 ml). The organic layer was washed with H$_2$O and saturated NaCl, dried over Na$_2$SO$_4$, filtered and stripped to leave a crude solid which was crystallized from AcOEt/hexane (1.4 g; 72% yield).

G. Boc—Nalψ[CH$_2$S]Ala—NH$_2$

Pseudopeptide Boc—Nalψ[CH$_2$S]Ala—OH (1.33 g; 3.4 mmol) was dissolved in THF (25 ml) and the solution was cooled to −30° C. Et$_3$N (0.48 ml; 3.4 mmol) was added, followed by isobutyl chloroformate (0.46 ml; 3.5 mmol). After 15 min an excess of NH$_3$ in CHCl$_3$ was added and the reaction was stirred for 30 min at −30° C. and at room temperature for 3 h. The solvent was removed in vacuo and the residue was dissolved in AcOEt (250 ml). The organic solution was washed with H$_2$O (1×50 ml), NaHCO$_3$ 5% (2×50 ml), H$_2$O (1×50 ml), 0.5M citric acid (2×50 ml) and saturated NaCl, then was dried over Na$_2$SO$_4$ and filtered. After evaporation in vacuo of AcOEt, the residue was crystallized from AcOEt/hexane (1.2 g; 90% yield).

H. HCl·H—Nalψ[CH$_2$S]Ala—NH$_2$

Pseudopeptide Boc—Nalψ[CH$_2$S]Ala—NH$_2$ (350 mg; 0.90 mmol) was dissolved in 4N HCl/dioxane and stirred at room temperature for 10 min. The solvent was removed in vacuo over KOH overnight, resulting in a thick, clear oil (280 mg; 96% yield).

I. HOHNCO—CH$_2$—CH(CH$_2$CH(CH$_3$)$_2$)—CO—Nal [CH$_2$S]Ala—NH$_2$

The product prepared in H is coupled with the 2-carbot-butoxycarbonyl-4-methylpentanoic acid and deprotacted in accordance with the procedure described in Example I. The product thereof was reacted with O-benzyl hydroxylamine followed by catalytic hydrogenation using an excess of catalyst in accordance with the procedure in Example I to generate the above compound.

EXAMPLE V

Preparation of
HONHCO—CH$_2$—CH(CH$_2$CH(CH$_3$)$_2$)—CO—Nalψ[CH$_2$NH]Ala—NH$_2$ A N$^\alpha$-tert-butyloxycarbonyl-N,O-dimethyl-2-naphthylalanine hydraxamic acid, (Boc—Nal—N-(OMe)Me), 1.

To a solution of N$^\alpha$-tert-butyloxycarbonyl-2-naphthylalanine (1.58 g, 5 mmol) in DMF (10 ml) N,O-dimethylhydroxylamine hydrochloride (0.54 g, 5.5 mmol) was added. The solution was then cooled to 0° C. and triethylamine (0.77 ml, 5.5 mmol) followed by EDC (1.05 g, 5.5 mmol) was added. The reaction mixture was stirred 2 h at 0° C. and 16 h at room temperature. The solvent was removed in vacuo and residue was partitioned in a separatory tunnel between ethyl acetate (70 ml) and 5% NaHCO₃ (20 ml). The organic layer was washed with 5% NaHCO₃ (2×20 ml), H₂O (1×20 ml), 1N HCl (1×20 ml), H₂O (1×20 ml) and NaHCO₃ (1×20 ml), and brine (1×20 ml). The ethyl acetate fraction was then dried over Na₂SO₄ and stripped to leave slightly yellow solid. Crystallization from ethyl acetate/hexane gave 1 (1.27 g, 71%): $R_f$ 0.80 (chloroform/methanol/acetic acid, 85:10:5), $R_f$ 0.54 (ethyl acetate/hexane, 1:1); m.p. 98°-100° C.; ¹H NMR (CDCl₃, 18° C.) δ 1.36 (9H, s, C(CH₃)₃), 3.07 (2H, m, CH₂), 3.17 (3H, s, N—CH₃) 3.66 (3H, s, O—CH₃), 5.04 (1H, m, CH), 5.20 (1H, d, NH), 7.30-7.77 (7H, m, C₁₀H₇).

B    N-tert-butyloxycarbonyl-2-naphthylalanylψ[CH₂NH]   alanine   amide   (Boc—Nalψ[CH₂NH]Ala—NH₂ 2 a.   N-tert-butyloxycarbonyl-2-naphthylalanal (Boc—Nal—CHO)

To a cold (0° C., ice bath) solution of N$^a$-tert-butyloxycarbonyl-N,O-dimethyl-2-naphthylalanine hydroxamic acid (0.54 g, 1.5 mmol) in THF (10 ml) LiAlH₄ (0.14 g, 3.75 mmol) was added in portions over 15 min. The resulting reaction mixture was stirred additionally 15 min at 0° C. followed by addition of ethyl acetate (100 ml) and 10% citric acid (80 ml). After stirring 0.5 h at 0° C., the layers were separated and the aqueous layer was extracted with ethyl acetate (3×50 ml). The organic fractions were pooled and washed with 5% NaHCO₃ (1×5 ml), H₂O (1×50 ml), 1N HCl (1×50 ml) and brine (1×50 ml), and dried over Na₂SO₄. Evaporation of solvent yielded white powder (0.43 g, 99%): $R_f$ 0.74 (ethyl acetate/hexane, 1:1); $R_f$ 0.58 (chloroform/methanol, 9:1), which was used immediately in the next step.

b.    N-tert-butyloxycarbonyl-2-naphthylalanylψ[CH₂NH]    alanine    amide    (Boc—Nalψ[CH₂NH]Ala—NH₂) 2

To a solution of N-tert-butyloxycarbonyl-2-naphthylalanal (0.43 g, 1.47 mmol) in methanol (4 ml) containing 3% acetic acid alanine amide hydrochloride (0.19 g, 1.5 mmol) was added. To the resulting mixture NaBH₃CN (0.12, 1.0 mmol) was added in portions over 0.5 h. After 2 h, when TLC (chloroform/methanol, 9:1) didn't show any substrates, the reaction mixture was partitioned in a separatory funnel between ethyl acetate (70 ml) and 5% NaHCO₃ (30 ml), and the aqueous fraction was extracted with ethyl acetate (3×20 ml). The organic fractions were pooled, washed with 5% NaHCO₃ (1×20 ml) and brine (1×20 ml). The organic layer was dried over Na₂SO₄, filtered and stripped to leave a yellow solid. The crude pseudodipeptide was purified by flash chromatography using 7% hexane in ethyl acetate.

Fractions containing the desired compound were pooled and stripped to leave white powder. Recrystallization from ethyl acetate/hexane gave 2 (0.319, 57%): $R_f$ 0.37 (chloroform/methanol, 9:1), $R_f$ 0.23 (chloroform/methanol/acetic acid, 85:10:5); m.p. 141°-143° C.; analytical RP-HPLC (t$_r$=36.08 min, a linear gradient of 5-65% B over 60 min at a flow rate of 1.0 ml/min); ¹H-NMR (CDCl₃, 18° C.) δ 1.29 (3H, d, CH—CH₃); 1.38 (9H, s, C(CH₃)₃), 2.67 (2H, octet, C₁₀H₇—CH₂), 2.95 (2H, d, CH₂—NH), 3.11 (1H, q, CH₃—CH), 4.05 (1H, m, NH—CH—CH₂), 4.52 (1H, d, CO—NH—CH), 5.28 (1H, m, CH₂—NH—CH), 7.03-7.83 (9H, m, C₁₀H₇ and CONH₂). C 2-Naphthylalanylψ[CH₂NH] alanine amide dihydrochloride (2 HCl×Nalψ[CH₂NH]Ala—NH₂) 3

N$^a$-tert-butyloxycarbonyl protected compound, 2 (0.19 g, 0.5 mmol) was placed in a round-bottom flask to which freshly prepared 4N HCl/dioxane (15 ml) was added. The solution was stirred for 1 h. Evaporation of solvent in vacuo yielded white, very hygroscopic powder (0.17 g, 100%): $R_f$ 0.22 (1-butanol/acetic acid/water, 4:1:1)), $R_f$ 0.05 (chloroform/methanol/acetic acid, 85:10:5) which was used immediately for the next step.

D.    HOHNCO—CH₂—CH(CH₂CH(CH₃)₂)—CO—Nalψ[CH₂NH]Ala—NH₂ 4

The product prepared in C is coupled with the 2-carbo-t-butyloxycarbonyl-4-methyl pentanoic acid and deprotected in accordance with the procedure described in Example I. The succinyl dipeptide is reacted with O-benzyl hydroxylamine followed by catalytic hydrogenation as described in Example I, giving a mixture of two diastereoisomers of the above compound.

EXAMPLE VI

Preparation of HON—CO—CH₂—CH(CH₂CH(CH₃)₂)—CO—DOPA—(Me)₂—Ala—NH₂

A. L-3,4-dihydroxyphenylalanine methyl ester hydrochloride, HCl·H—Dopa—OMe

To the cooled to −10° C. suspension of L-3,4-dihydroxyphenylalanine in 30 m of absolute methanol, thionyl chloride (2.6 ml, 36 mM) was added dropwise. The reaction mixture was stirred at room temperature for 48 h. Then, methanol was evaporated under reduced pressure and the remaining residue was treated three times with ethyl ether evaporating after each time. Finally, the product was crystallized from the methanol/ethyl ether mixture, giving 7.43 g 100% white crystalline substance.

NMR: (300 MHz, CDCl₃)

δ (ppm) 1.4 (9H, s, (CH₃)₃—C); 2.05 (2H, m, CH₂β); 3.70 (3H, s, CH₃ ester); 384 (6H, s, CH₃O); 4.54 (1H, m, CHα), 4.95 (1H, m, NH); 6.62 (2H, d, CH$_{nrom}$); 6.78 (1H, d, CH$_{nrom}$).

B. N-t-Butyloxycarbonyl-L-3,4-dihydroxyphenylalanine methyl ester, Boc—Dopa—OMe

To a solution of L-3,4-dihydroxyphenylalanine methyl ester hydrochloride (7.43 g, 30 mM) and 4.2 ml 30 mM of triethylamine in 80 ml of t-butanol was added portionwise di-t-butyl pyrocarbonate (6.5 g, 3 mM). The reaction mixture was stirred for 1 h and then t-butanol was removed under reduced pressure. The remaining oily residue was dissolved in 250 ml of ethyl acetate and washed with 5% NaHCO₃(3 x), H₂O (1 x), 0.5 citric acid (3 x) and H₂O (1 x), and dried over Na₂SO₄. After removal of the ethyl acetate, the compound was crystallized from the benzene giving 8.81 g (94%) white crystalline product. mp=129°-131° C.

C. N-t-butyloxycarbonyl-L-3,4-dimethoxyphenylalanine methyl ester, Boc—Dopa(Me)₂—OMe The mixture of Boc—Dopa—OMe (3.1 g, 10 mM), potassium carbonate (1.52 g, 11 mM), 18-crown-6 (291 mg, 1.1 mM), dimethylsulfate (1.05 ml, 11 mM) in 10% DMF in benzene was heated under reflux in a round bottom flask equipped with azeotropic distilling receiver. After 4 h of reflux, fresh portions of potassium carbonate (0.75 g, 5 mM) and dimethyl sulfide (0.5 ml, 0.5 ml) were added and the resulting reaction mixture was reflux for an additional 4 h. Then the reaction mixture was cooled and 100 ml of cold water was added. The organic layer was washed 3 x with H₂O and dried over Na$_2$SO$_4$. Crystallization from benzene gave 1.92 g (52%) solid product.

mp=109°–111° C.

R$_f$=0.84, (nBuOH:AcOH;H$_2$O, 4:1:1, v/v)

NMR (300 MHz, CCl$_3$)

δ (ppm) 1.4 (9H, s, (CH$_3$)$_3$—C); 2.05 (2H, m, CH$_2$β); 3.70 (3H, s, CH$_3$ ester); 3.84 (6H, s, CH$_3$O—); 4.54 (1H, m, CHα), 4.95 (1H, s, NH); 6.62 (2H, d, CH$_{arom}$); 6.78 (1H, d, CH$_{arom}$).

D. N-t-butyloxycarbonyl-L-3,4-dimethoxyphenylalanine, Boc—Dopa(Me)$_2$—OH

To a solution of Boc—Dopa(Me)$_2$—OMe (1.71 g, 4.6 mM) in 25 ml of MeOH was added 8 mM of NaOH in 5 ml of water and the resulting mixture was stirred for 40 min. Then methanol was evaporated under reduced pressure and the remaining mixture was diluted with 80 ml of water. The solution was acidified to pH=2 in 1N HCl and the product was extracted with AcOEt (3×50 ml). Combined ethyl acetate solution was washed twice with water and then dried over Na$_2$SO$_4$, filtered and evaporated. The oily residue was crystallized from ether/hexane giving 1.19 g white solid product.

mp=140°–147° C., TLC R$_f$=0.94 (CHCl$_3$:MeOH:AcOH, 85:10:5); R$_f$=0.81 (n-BuOH:AcOH:H$_2$O, 4:1:1, v/v)

NRM: (CDCl$_3$, 300 MHz)

δ (ppm): 1.42 (9H, s, (CH$_3$)$_3$C); 3.1 (2H, m, CH$_2$β); 3.84 (6H, s, CH$_3$O); 4.58 (1H, m, CHα); 4.84 (1H, d, NH); 6.76 (4H, m, CH$_{nrom}$).

E. Boc—Dopa(Me)$_2$—Ala—NH$_2$

To the chilled (0° C.) solution of Boc—Dopa(Me)$_2$—OH (1.025 g) N-hydroxybenzotriazole (0.40 g) and alanine amide hydrochloride (0.385 g) in a mixture of dichloromethane/DMF (8:1 v/v) was added triethylamine (0.42 ml) and then portionwise N-ethyl-N$^1$-(3-dimethyl amino propyl) carbodiimide (0.575 g) over 30 min. The reaction mixture was stirred for 2 h at 0° C. and overnight at RT. The next day, ethyl acetate (200 ml) was added and the solution was washed three times with 50 ml of 1N HCl, NaHCO$_3$ (sat), brine, and dried over Na$_2$SO$_4$. Evaporation of solvent gave 0.95 g of white material.

TLC: R$_f$=0.92 (CHCl$_3$:MeOH:AcOH, 85:10:5); R$_f$=0.79 (n-BuOH:AcOH:H$_2$O, 4:1:1).

F. HCl·H—DOPA(Me)$_2$—Ala—NH$_2$

The product of E is dissolved in 4N-HCl/dioxane and stirred at room temperature for approximately 10–15 minutes. The solvent is removed in vacuo KOH overnight to form the above product.

G.

A N$^α$-tert-butyloxycarbonyl-N,O-dimethyl-phenylalanine hydroxamic acid (Boc—Phe—N-(OMe)Me) 5

The title compound was synthesized from tert-butyloxycarbonyl-L-phenylalanine (2.65 g, 0.1 mmol) and N,O-dimethylhydroxylamine hydrochloride (1.07 g, 11 mmol) according to the procedure given for 1. The synthesis yielded compound 5 as an oil (2.48 g, 81%): R$_f$0.40 (ethyl acetate/hexane, 1:1), R$_f$0.78 (chloroform/methanol/acetic acid, 85:10:5); $^1$H-NMR (CDCl$_3$, 17° C.) δ 1.38 (9H, s, C(CH$_3$)$_3$, 3.05 (2H, m, CH$_2$), 3.18 (3H, s, N—CH$_3$), 3.66 (3H, s, O—CH$_3$), 4.97 (1H, m, CH), 5.18 (1H, d (br.), NH), 7.17–7.28 (5H, m, C$_6$H$_5$).

B N-tert-butyloxycarbonyl-phenylalanylψ[CH$_2$NH] alanine amide (Boc—Pheψ[CH$_2$NH]Ala—NH$_2$) 6 a. N-tert-butyloxycarbonyl-phenylalanal (Boc—Phe—CHO)

The title aldehyde was synthesized from N$^α$-tert-butyloxycarbonyl-N,O-dimethyl-phenylalanine hydroxamic acid (0.92 g, 3 mmol) by reduction using LiAlH$_4$ (0.28 g, 7.5 mmol) according to the procedure given for 2. Evaporation of ethyl acetate yielded a white powder (0.55 g, 73%): R$_f$0.70 (ethyl acetate/hexane, 1:1), R$_f$ 0.53 (chloroform/methanol, 9:1), which was used immediately in the next step.

b. N-tert-butyloxycarbonyl-phenylalanylψ[CH$_2$NH] alanine amide (Boc—Pheψ[CH$_2$NH]Ala—NH$_2$) 6

Compound 6 was prepared from N-tert-butyloxycarbonyl-phenylalanal (0.5 g, 2 mmol) and alanine amide hydrochloride (0.26 g, 2 mmol) by following the procedure described for 2. Crude product was purified by flash chromatography using ethyl acetate as mobile phase.

Fractions containing the desired compound were pooled and stripped to leave white powder. Recrystallization from ethyl acetate/hexane gave 6 (0.39 g, 62%): R$_f$ 0.30 (chloroform/methanol, 9:1), R$_f$ 0.20 (chloroform/methanol/acetic acid, 85:10:5); m.p. 138°–140° C.; analytical RP-HPLC (t$_r$=12.84 min, a linear gradient of 20–60% B over 40 min at a flow rate of 1.0 ml/min); $^1$H-NMR (CDCl$_3$, 17° C.) δ 1.25 (3H, d, CH—CH$_3$), 1.37 (9 h, s, C(CH$_3$)$_3$), 2.58 (2H, octet, C$_6$H$_5$—CH$_2$), 2.75 (2H, d, CH$_2$—NH), 3.07 (1H, q, CH$_3$—CH), 4.00 (1H, m, NH—CH—CH$_2$), 4.55 (1H, d, CO—NH—CH), 5.41 (1H, s, CH$_2$—NH—CH), 7.02–7.29 (7H, m, C$_6$H$_5$ and CO—NH$_2$).

C Phenylalanylψ[CH$_2$NH] alanine amide dihydrochloride (2 HCl × Pheψ[CH$_2$NH] 7

N-tert-butyloxycarbonyl protection was removed

H
HON—COCH$_2$—CH(CH$_2$—CH(CH$_3$)$_2$)—CO—DOPA(Me)$_2$—Ala—NH$_2$

The product prepared in F is coupled with the 2-carbot-butoxycarbonyl-4-methyl pentanoic acid and deprotected in accordance with the procedure described in Example I. The product thereof is coupled with O-benzyl hydroxylamine followed by catalytic hydrogenation in accordance with the procedure described in Example I to give the above-identified compound.

EXAMPLE VII from N-tert-butyloxycarbonyl-phenylalanyl ψ[CH$_2$NH] alanine amide (0.3 g, 0.95 mmol) using 4N HCl/dioxane following the procedure given for 3. Evaporation of solvents gave white hygroscopic solid, 7 (0.28 g, 100%): R$_f$0.20 (1-butanol/acetic acid/water, 4:1:1), R$_f$ 0.40 (chloroform/methanol/acetic acid, 85:10:5) which was used immediately in the next step.

D. HONHCO—CH$_2$—CH(CH$_2$CH(CH$_3$)$_2$)—CO—Phe ψ[CH$_2$NH]Ala—NH$_2$

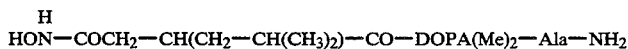

Preparation of HONHCO—CH$_2$—CH(CH$_2$CH)(CH$_3$)$_2$)—CO—PheΨ[CH$_2$N]Ala—NH$_2$ The product prepared in C is coupled with 2-carbo-t-butyloxy-carbonyl-4-methyl pentanoic acid followed by O-benzyl hydroxylamine and the product hydrogenated in accordance with the procedure described in Example I.

EXAMPLE VIII

Preparation of HONHCO—CH$_2$—CH(CH$_2$CH(CH$_3$)$_2$)—CO—Tyr(Me)ψ[CH$_2$NH]Ala—NH$_2$ A N$^\alpha$tert-butyloxycarbonyl-(N,O$^1$,O$^2$-trimethyl)-tyrosine hydroxamicacid (Boc—Tyr(Me)—N-(OMe)Me) 9

The title compound was prepared from N$^\alpha$-tert-butyloxycarbonyl-(O-methyl)tyrosine (2.95 g, 10 mmol) and N,O-dimethylhydroxylamine hydrochloride (1.07 g, 11 mmol) by following the procedure given for 1. Recrystallization from ethyl acetate/benzene/hexane gave white crystals (2.90 g, 85%): m.p. 59°–61° C.; R$_f$ 0.45 (ethyl acetate/hexane, 1:1), R$_f$ 0.78 (chloroform/methanol/acetic acid, 85:10:5); $^1$H-NMR (CDCl$_3$, 18° C.) δ 1.38 (9H, s, C(CH$_3$)$_3$), 2.97 (2H, m, CH$_2$), 3.16 (3H, s, N—CH$_3$), 3.65 (3H, s, N—O—CH$_3$), 3.76 (3H, s, C—O—CH$_3$), 4.91 (1H, m, CH), 5.13 (1H, d, NH), 6.80-7.08 (4H, dd, C$_6$H$_4$).

B N-tert-butyloxycarbonyl-(0-methyl)-tyrosalψ[CH$_2$NH] alanine amide (Boc-Tyr-(OMe)ψ[CH$_2$NH]Ala—NH$_2$) 10 a. N-tert-butyloxycarbonyl-(0-methyl)tyrosyl (Boc—Tyr(Me)—CHO)

The title compound was synthesized from N$^\alpha$-tert-butyloxycarbonyl-(N,O$^1$,O$^2$-trimethyl)tyrosine hydroxamic acid (1.02 g, 3 mmol) and LiAlH$_4$ (0.28 g, 7.5 mmol) according to the procedure described for 2. Evaporation of ethyl acetate gave white powder (0.80 g, 95%): R$_f$ 0.72 (ethyl acetate/hexane, 1:1), R$_f$ 0.55 (chloroform/methanol, 9:1), which was used immediately in the next step.

b. N-tert-butyloxycarbonyl-(O-methyl)-tyrosylψ[CH$_2$NH] alanine amide (Boc—Tyr-(OMe)ψ[CH$_2$NH]Ala—NH$_2$) 10

Pseudodipeptide 10 was prepared from N-tert-butyloxycarbonyl-O-methyl-tyrosal (0.8 g, 2.87 mmol) alanine amide hydrochloride (0.32 g, 2.5 mmol) by following the procedure given for 2. Crude product was purified by flash chromatography using ethyl acetate as mobile phase. Fractions containing the desired compound were pooled and stripped to leave a white powder. Recrystallization from ethyl acetate/hexane gave 10 (0.51 g, 59%): R$_f$ 0.32 (chloroform/methanol, 9:1), R$_f$ 0.21 (chloroform/methanol/acetic acid, 85:10:5); m.p. 122°–124° C.; analytical RP-HPLC (t$_r$=12.98, a linear gradient of 20–60% B over 40 min at a flow rate of 1.0 ml/min); $^1$H-NMR (CDCl$_3$, 18° C.) δ 1.26 (3H, d, CH—CH$_3$), 1.38 (9H, s, C(CH$_3$)$_3$), 2.58 (2H, octet, C$_6$H$_4$—CH$_2$), 2.71 (2H, d, CH$_2$—NH), 3.08 (1H, q, CH$_3$—CH), 3.77 (3H, s, O—CH$_3$), 3.88 (1H, m, NH—CH—CH$_2$), 4.49 (1H, d, CO—NH—CH) 5.56 (1H, bs, CH$_2$—NH—CH), 6.80-7.24 (6H, m, C$_6$H$_4$ and CO—NH$_2$).

C (O-Methyl)tyrosylψ[CH$_2$NH] alanine amide dihydrochloride (2 HCl×Tyr(OMe)ψ[CH$_2$NH]Ala—NH$_2$) 11

The title compound was synthesized from N-tert-butyloxycarbonyl-(O-methyl)tyrosylψ[CH$_2$NH] alanine amide (0.25 g, 0.71 mmol) using 4N HCl/dioxane according to the procedure described for 3. Evaporation of solvents and drying in vacuo gave hygroscopic white powder, 11 (0.23 g, 100%): R$_f$ 0.20 (1-butanol/acetic acid/water, 4:1:1), R$_f$ 0.40 (chloroform/methanol/acetic acid, 85:10:5), which was used immediately in the next step.

D. HONHCO—CH$_2$—CH(CH$_2$CHCCH$_3$)$_2$)—CO—Tyr(Me)ψ[CH$_2$NH]Ala—NH$_2$

The product in C is coupled with 2-carbo-t-butyloxycarbonyl-4-methyl pentanoic acid, followed by O-benzyl hydroxyl amine and the product is hydrogenated in accordance with the procedure described in Example I.

EXAMPLE IX

Using the procedures described herein, the following compounds can be prepared:

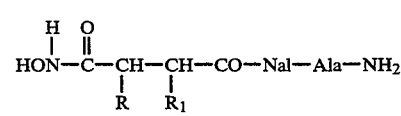
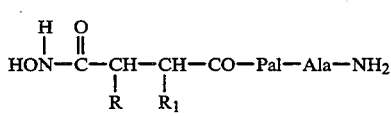
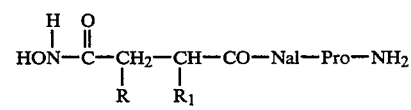
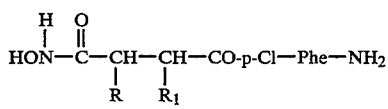
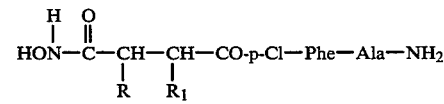
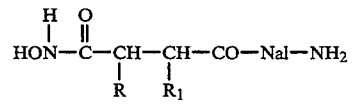
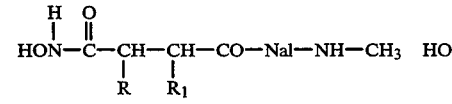
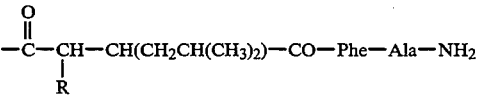
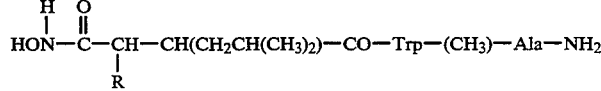

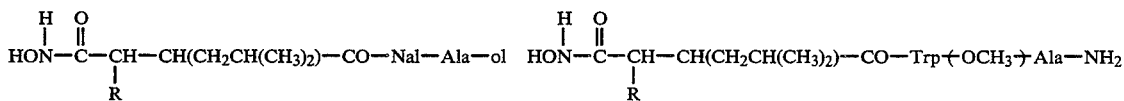
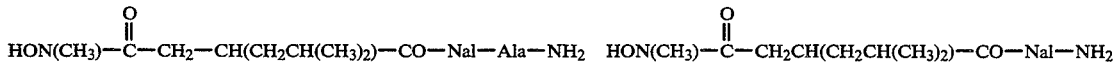
wherein
Pal=2, 3 or 4-pyridylalanine
Nal=1- or 2-naphthylalanine
Trp(CH₃)=methyl substituted tryptophan
Trp(OCH₃)=methoxy substituted tryptophan
$R_1 = CH_2CH(CH_3)_2$ or $CH(CH_3)CH_2CH_3$
$R = H$ or $CH_3$
EXAMPLE X
Using the procedures described herein, the following compounds can also be prepared.
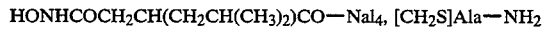
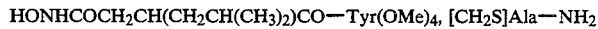
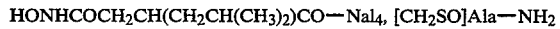
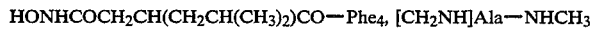
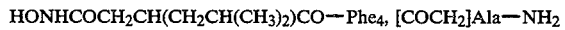
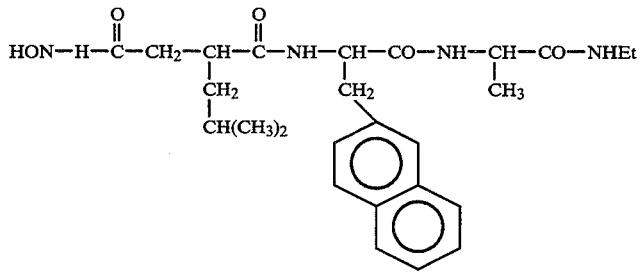
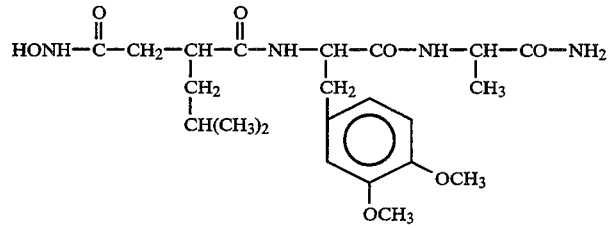
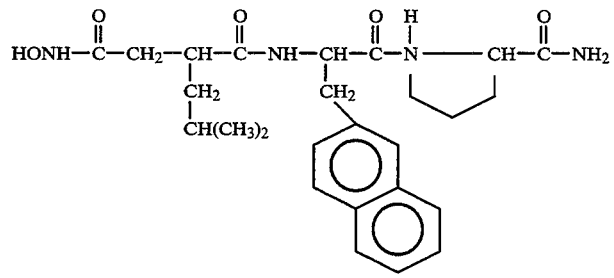

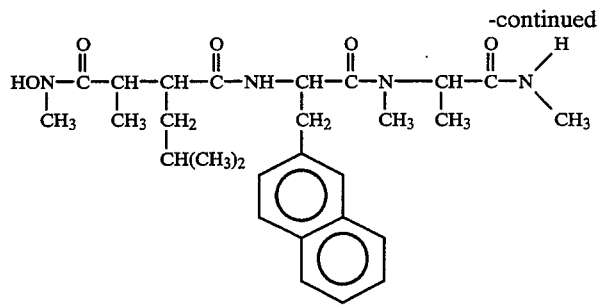
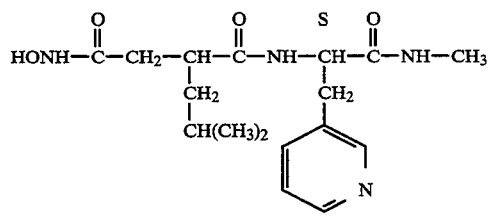
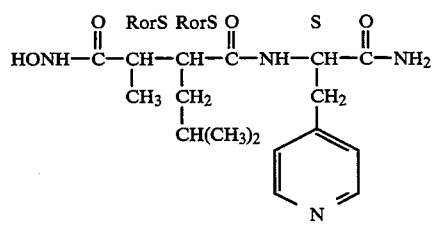
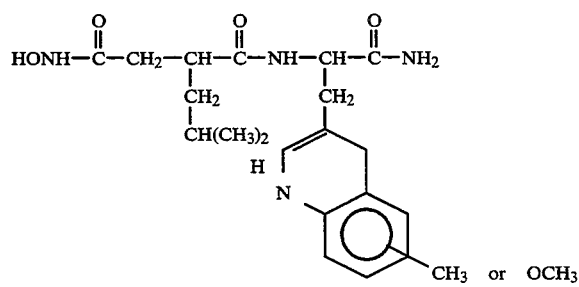
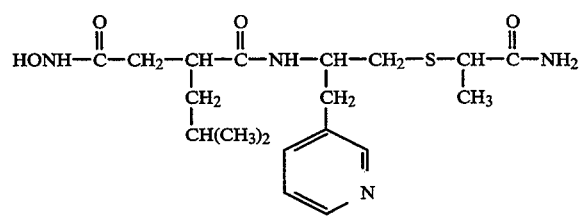
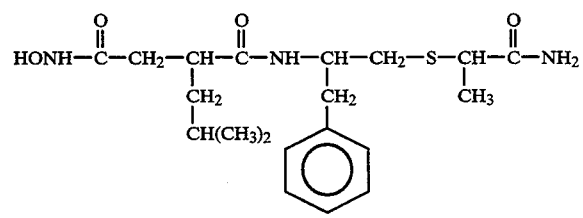
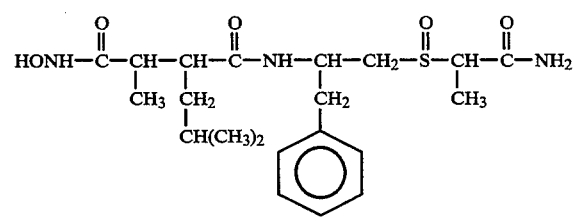

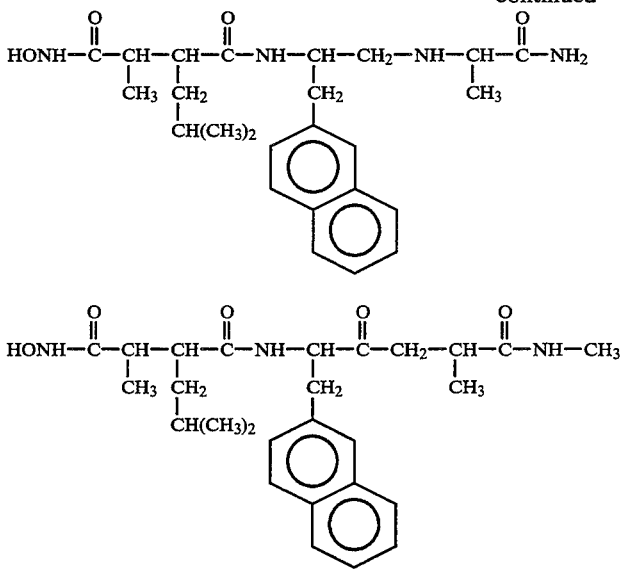

The compounds of the present invention are inhibitors of mammalian collagenase. They are believed to bind to mammalian collagenase. More specifically, they are believed to bind to the active metal, i.e., zinc in collagenase.

The compounds of the present invention are inhibitors of collagenase. The effectiveness of a compound's inhibition by collagenase is shown by the following assay:

Assay Procedures

Porcine synovial collagenase activity (PSC) was measured with type I collagen essentially as described by Darlak et al. (1990). Varying amounts of inhibitor were added to the acid-soluble calf skin collagen (0.8 $\mu$M) at 35° C. in 0.05M tris-HCl, 0.2M NaCl, 5 mM $CaCl_2$, 0.25M glucose, pH 7.7. Collagen degradation was initiated by adding purified porcine synovial collagenase and the reactions were stopped by the addition of an equal volume of sample dilution buffer (Laemmli, 1970) followed by boiling for 2–3 min. Undegraded collagen was resolved from its degradation products by polyacrylamide slab gel electrophoresis as described by Laemmli (1970). The gels were fixed in isopropanol/acetic acid/water (100:40:300 v/v) and then stained with 1% Coomassie Blue R-250 in fixing solution. After destaining, the percentage of $\alpha 1$ chain converted to the corresponding TC fragment was estimated by densitometry using a Bio-Rad model 610 video densitometer. IC50 values were estimated from the dependence of the percent of collagen degraded on inhibitor concentration.

Recombinant human fibroblast collagenase (rHFC) and porcine synovial gelatinase (PSG) were assayed at 37° C. by the procedure of Stack and Gray (1989). The fluorogenic metalloproteinase substrate Dnp-Pro-Leu-Gly-Leu-Trp-Ala-D-Arg-$NH_2$ was dissolved at an initial concentration of 10 $\mu$M in 0.05M tris-HCl, 0.2M NaCl, 5 mM $CaCl_2$, pH 7.7. Hydrolysis of the substrate at the Gly-Leu bond results in an increase in fluorescence that was monitored using an SLM-500C spectrofluorometer with excitation at 280 nm and emission at 346 nm. The reaction was initiated by addition of the enzyme; after determining the initial rate of substrate hydrolysis an aliquot of inhibitor was added and the inhibited rate redetermined. For lower affinity inhibitors (IC50>>[$E_0$], where $E_0$ is the enzyme concentration), inhibitor potencies were determined from plots of log ($A_0/A_i - 1$) vs. log [Inhibitor], where $A_0$ is the activity measured in the absence of inhibitor and $A_i$ is that measured in the presence of inhibitor at concentration i (Ambrose et al., 1950). For high affinity inhibitors (IC50=[$E_0$]) only an upper limit of inhibitor potency could be estimated (Dixon and Webb, 1979).

Ambrose, J. F. Kistiakowski, G. B., and Kridl, A. G. (1950) J. Am. Chem. Soc. 72, 317–321.

Darlak, K., Miller, R. B., Stack, M. S., Spatola, A. F., and Gray, R. D. (1990) J. Biol. Chem. 265, 5199–5205.

Dixon, M., and Webb, E. C. (1979) Enzymes, Third Edition, New York, Academic Press, pp. 361–368.

Laemmli, U. K. (1970) Nature (London) 227, 680–685.

Stack, M. S., and Gray, R. D. (1989) J. Biol. Chem. 264, 4277–4281. The results are indicated in the table hereinbelow.

TABLE I

Inhibition of MMPs by hydroxamic acid derivatives $P_1^-$—$P_2^-$—$P_3^-$

| # | $P_1^*$ | $P_2^*$ | $P_3^*$ | PSC/CSC | PSC/FS-7 | PSG/FS-7 | rHFC/FS-7 |
|---|---------|---------|---------|---------|----------|----------|-----------|
| 1 | H4[ONHCO]—DL—Leu | Phe—$NH_2$ | | | 250 | 700 | |
| 2 | | Trp—$NH_2$ | | | 180 | 370 | |
| 3 | | Phe | Ala—$NH_2$ | | 60 | | |
| 4 | | Trp | Ala—$NH_2$ | | 60 | | |
| 5 | | Hal | Ala—$NH_2$ | | 25–30 | 21 | |
| 6 | | Hal—$NH_2$ | | 100–300 | 350 | | |
| | | | | 30–100 | 71 | | |

TABLE I-continued

Inhibition of MMPs by hydroxamic acid derivatives $P_1^- - P_2^- - P_3^-$

| # | $P_1$* | $P_2$* | $P_3$* | IC$_{50}$ ($\mu$M) PSC/CSC | PSC/FS-7 | PSG/FS-7 | rHFC/FS-7 |
|---|---|---|---|---|---|---|---|
| 7 | | I'-Hal—NH$_2$ | | 300–500 | 280 | | |
| | | | | 300–500 | 280 | | |
| 8 | H4[ONHCOCH$_2$]—DL—Leu | Trp—NH$_2$ | | | | <0.0001 | 0.0025 |
| | | | | | | 0.5 | 2.2 |
| 9 | | Hal | Ala—NH$_2$ | 0.017 | 0.005 | <0.0001 | |
| | | | | 0.46 | 0.45 | 0.16 | |
| 10 | | Trp | Ala—NH$_2$ | 0.001 | 0.006 | 0.002 | |
| | | | | 0.5 | 0.24 | 0.17 | |
| 11 | | pClPhe | Ala—NH$_2$ | | | 0.07 | 0.14 |
| | | | | | | 4.5 | 2.5 |
| 12 | | Hal | Pro—NH$_2$ | 0.01–.03 | | 0.0032 | 0.032 |
| | | | | 1–3 | 1.1 | 0.1 | 1.6 |
| 13 | | Hal | Ala—NH$_2$ | 0.01–.03 | | | |
| | | | | 0.1–0.3 | | | |
| 14 | | Dopa(OMe)$_2$ | Ala—NH$_2$ | 0.03–0.1 | 0.01 | 0.004 | |
| | | | | 1–3 | 2.8 | 1.3 | |
| 15 | | Hal | Ala—NHCH$_2$ | | | <0.001 | 0.016 |
| | | | | | | 0.028 | 1.0 |
| 16 | H4[ONHCOCH(CH$_3$)]—DL—Leu | Phe | Ala—NH$_2$ | 1 | | 10 | 10 |
| | | | | >3 | | 13 | 17 |
| 17 | | Hal | Ala—NH$_2$ | 0.1–0.3 | | 0.3 | 0.35 |
| | | | | 0.1–0.3 | | 0.6 | 0.4 |
| | | | | 0.1 | | 0.4 | 0.6 |
| | | | | 0.3 | | 0.45 | 2.0 |
| 18 | | Trp | Ala—NH$_2$ | 0.3 | | 0.1 | 0.18 |
| | | | | 0.1 | | 0.7 | 0.46 |
| | | | | 0.3 | | 0.5 | 0.7 |
| 19 | H4[OH(CH$_3$)COCH$_3$]—DL—Leu | Phe | Ala—NH$_2$ | 10–30 | | | |
| | | | | 300–500 | | | |

*Where more than one IC$_{50}$ value is shown, the first is for the diastereomer of higher mobility on a C18 reversed phase column and the second is for the diastereomer of slower mobility. For compounds 16–18, there are two asymmetric centers and therefore four isomers. For 16, two of these were resolved; for 18, three isomers were resolved. Where a range of IC$_{50}$ values is given, 50% inhibition was between the indicated values. Abbreviations: PSC = pig synovial collagenase; PSG = pig synovial gelatinase; rHFC = recombinant human fibroblast collagenase; CSC = calf skin collagen as substrates; FS-7 = DnpPLGLWA-o-R-NH$_2$. Assays utilizing collagen were carried out as described in Darlak, K., Miller, R. B., Stack, H. S., Spatola, A. F., Gray, R. D. (1990) J. Biol. Chem. 265, 5199–5205; assays utilizing FS-7 were carried out as described in Stack, H. S., Gray. R. D. (1989) J. Biol. Chem. 64, 4277–4281. A "blank" entry indicates that the compound was not assayed.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only be the appended claims.

What is claimed is:

1. A compound of the formula:

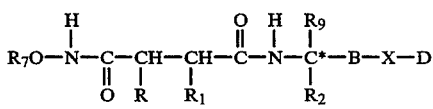

or pharmaceutically acceptable salts thereof
wherein R and $R_1$ are independently hydrogen, lower alkyl, aryl or aryl lower alkyl, $R_2$ is aryl lower alkyl, said $R_2$ being unsubstituted or mono- or di-substituted with halo, nitro, carboxy, lower carbalkoxy, cyano, lower alkanoyl, trifluoromethyl, lower alkyl, hydroxy, lower alkoxy, formyl, amino, lower alkyl amino, di-lower alkyl amino, mercapto, lower alkylthio or mercapto lower alkyl, B is

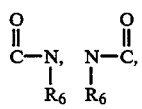

$CH_2SO$, $CH_2SO_2$,

$CH_2S$, $COCH_2$, $CH=CH$,

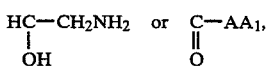

$AA_1$ is an amino acid residue,
X is a chemical bond, lower alkylene,

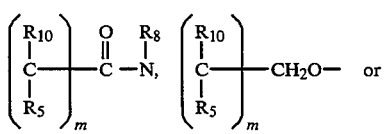

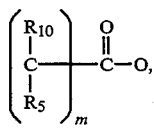

$R_9$ and $R_{10}$ are independently hydrogen, methyl or ethyl, $R_5$, $R_6$, $R_7$ and $R_8$ are independently hydrogen or lower alkyl, D is hydrogen or lower alkyl which is unsubstituted or substituted with halo, nitro, carboxy, lower carbalkoxy, cyano, lower alkanoyl, trifluoromethyl, lower alkyl, hydroxy, lower alkoxy, formyl, amino, lower alkyl amino, diloweralkylamino, mercapto, lower alkyl thio, mercapto lower alkyl or aryl, m is 1, 2 or 3 with the proviso that when B is

and X is a chemical bond or lower alkylene, then $R_2$ is not unsubstituted benzyl or benzyl monosubstituted with hydroxy or lower alkoxy and with the further proviso that when B is

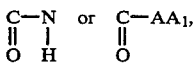

and X is

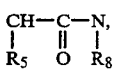

then $R_2$ is not unsubstituted benzyl or benzyl substituted with hydroxy or lower alkoxy.

2. The compound according to claim 1 wherein B is $CH_2S$, $CH_2SO$,

$CH_2SO_2$,

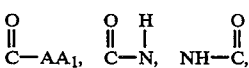

or $COCH_2$.

3. The compound according to claim 2 in which B is $CH_2S$, $CH_2SO$, $CH_2NH$, or $CH_2SO_2$.

4. The compound according to claim 2 in which B is $CH_2S$, $CH_2SO$, $CH_2NH$, $CH_2SO_2$,

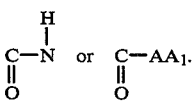

5. The compound according to claim 1 in which $R_2$ is unsubstituted or substituted

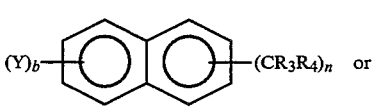

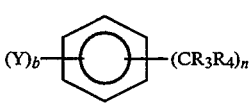

wherein $R_3$ and $R_4$ are independently hydrogen or lower alkyl and n is 1–3 and Y is hydrogen lower alkyl or lower alkoxy and b is 1 or 2.

6. The compound according to claim 5 in which n is 1 and $R_2$ and $R_4$ are hydrogen.

7. The compound according to claim 1 in which $R_3$ and $R_4$ are hydrogen and n is 1.

8. The compound according to claim 1 in which $R_7$ is hydrogen.

9. The compound according to claim 1 in which R is hydrogen or methyl.

10. The compound according to claim 1 in which $R_1$ is isobutyl or sec-butyl.

11. The compound according to claim 1 in which X-D is

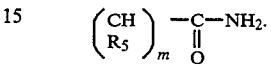

12. The compound according to claim 1 in which B is $CH_2S$, $CH_2SO$,

$CH_2SO_2$,

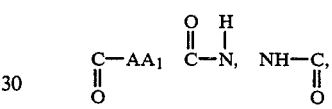

or $COCH_2$ and $R_7$ is H.

13. The compound according to claim 1 in which X-D is

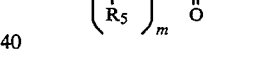

and B is $CH_2S$, $CH_2SO$, $CH_2NH$ or $CH_2SO_2$.

14. The compound according to claim 12 in which B is $CH_2S$, $CH_2SO$, $CH_2NH$, $CH_2SO_2$,

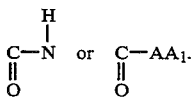

15. The compound according to claim 8 in which $R_7$ is hydrogen and $R_2$ is unsubstituted or substituted

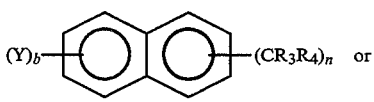

wherein $R_3$ and $R_4$ are independently hydrogen or lower alkyl and n is 1–3 and Y is hydrogen lower alkyl or lower alkoxy and n is 1 or 2.

16. The compound according to claim 15 in which n is 1 and $R_3$ and $R_4$ are hydrogen.

17. The compound according to claim 1 in which $R_7$ is hydrogen and R is hydrogen or methyl.

18. The compound according to claim 1 in which $R_7$ is hydrogen and $R_1$ is isobutyl or sec-butyl.

19. The compound according to claim 1 in which $R_7$ is hydrogen and X-D is

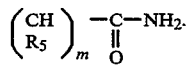

20. The compound according to claim 1 in which $R_7$ is hydrogen and R is hydrogen or methyl and $R_1$ is isobutyl.

21. The compound according to claim 1 in which R is hydrogen or methyl, $R_1$ is isobutyl, $R_7$ is hydrogen and B is $CH_2S$, $CH_2SO$, $CH_2NH$, $CH_2SO_2$,

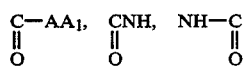

or $COCH_2$.

22. The compound according to claim 21 in which B is $CH_2S$, $CH_2SO$, $CH_2NH$ or $CH_2SO_2$.

23. The compound according to claim 22 in which B is $CH_2S$, $CH_2SO$, $CH_2NH$, $CH_2SO_2$,

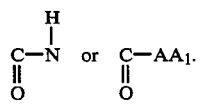

24. The compound according to claim 1 in which R is hydrogen or methyl, $R_1$ is isobutyl, $R_7$ is hydrogen and $R_2$ is

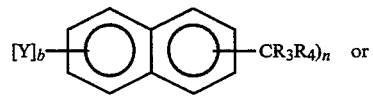

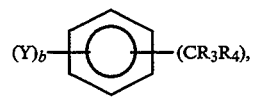

wherein $R_3$ and $R_4$ are independently hydrogen or lower alkyl, n is 1-3, and Y is hydrogen, lower alkyl or lower alkoxy and b is 1 or 2.

25. The compound according to claim 24 in which n is 1 and $R_2$ and $R_4$ are hydrogen.

26. The compound according to claim 1 in which R is hydrogen or methyl, $R_1$ is isobutyl, $R_7$ is hydrogen, and X-D is

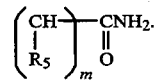

27. The compound according to claim 1 in which R and $R_1$ are independently hydrogen, lower alkyl, aryl or aryl lower alkyl,
B is

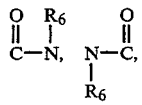

$CH_2SO$, $CH_2SO_2$,

$COCH_2$, $CH=CH$,

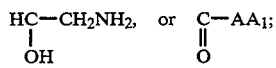

$AA_1$ is an amino acid residue,
X is a chemical bond, lower alkylene

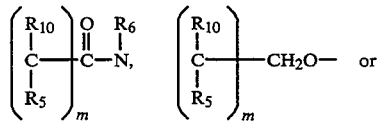

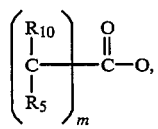

$R_9$ and $R_{10}$ are independently hydrogen, methyl or ethyl,
D,$R_5$, $R_6$ and $R_9$ are independently hydrogen or lower alkyl,
m is 1, 2 or 3, and $R_2$ is

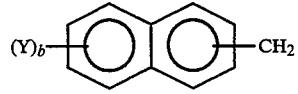

wherein Y is hydrogen, halo, nitro, carboxy, lower carbalkoxy, cyano, lower alkaroyl, trifluoromethyl, lower alkyl, hydroxy, lower alkoxy, formyl, amino, lower alkyl amino, di-lower alkylamino, mercapto, lower alkylthio, or mercapto lower alkyl and b is 1 or 2.

28. The compound according to claim 27 in which $R_2$ is hydrogen or lower alkyl and b is 1.

29. The compound according to claim 27 in which $R_2$ is

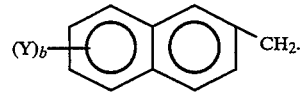

30. The compound according to claim 27 in which B is $CH_2S$, $CH_2SO$,

CH₂SO₂, $$\underset{O}{\overset{}{C}}-AA_1, \quad \underset{O}{\overset{H}{\underset{\|}{C}-N}}, \quad \underset{O}{\overset{}{NH-\underset{\|}{C}}},$$

or COCH₂.

31. The compound according to claim 30 in which B is CH₂S, CH₂SO, CH₂NH or CH₂SO₂.

32. The compound according to claim 27 in which B is CH₂S, CH₂SO, CH₂NH, CH₂SO₂, $$\underset{O}{\overset{H}{\underset{\|}{C}-N}} \quad \text{or} \quad \underset{O}{\overset{}{\underset{\|}{C}-AA_1}}.$$

33. The compound according to claim 27 in which R is hydrogen or methyl.

34. The compound according to claim 27 in which R₁ is isobutyl or sec-butyl.

35. The compound according to claim 27 in which X-D is $$\left(\underset{R_5}{\overset{}{CH}}\right)_m \underset{O}{\overset{}{\underset{\|}{C}-NH_2}}.$$

36. The compound according to claim 27 in which R is hydrogen or methyl, and R₁ is isobutyl.

37. The compound according to claim 27 in which B is CH₂S, CH₂SO, $$\overset{H}{\underset{}{CH_2N}},$$

CH₂SO₂, $$\underset{O}{\overset{}{\underset{\|}{C}-AA_1}}, \quad \underset{O}{\overset{}{\underset{\|}{C}-NH}}, \quad \underset{O}{\overset{}{\underset{\|}{NHC-}}}$$

or COCH₂, R is hydrogen or methyl and R₁ is isobutyl.

38. The compound according to claim 27 in which B is CH₂S, CH₂SO, CH₂NH, CH₂SO₂, $$\underset{O}{\overset{H}{\underset{\|}{C-N}}} \quad \text{or} \quad \underset{O}{\overset{}{\underset{\|}{C-AA_1}}},$$

R is hydrogen or methyl and R₁ is isobutyl.

39. The compound according to claim 1 in which R₇ is hydrogen and R₂ is (Y)$_b$—⬡—CH₂ wherein Y is lower alkyl, halo or lower alkoxy, and b is 1 or 2.

40. The compound according to claim 39 in which R₂ is (Y)—⬡—CH₂.

41. The compound according to claim 39 in which R₂ is DOPA(OMe)₂.

42. The compound according to claim 1 having the configuration around the chiral centers are in the S or R form.

43. The compound according to claim 1 in which the configuration around the asterisked carbon is S.

44. The compound according to claim 1 which is

HONH—$\underset{O}{\overset{}{\underset{\|}{C}}}$—CH₂CH(CH₂CH(CH₃)₂)—CO-naphthyl-Nal—Ala—NH₂.

45. The compound according to claim 1 which is HO—NH—CO—CH₂—CH—(CH₂—CH(CH₃)₂—CO—Nal—Pro—NH₂.

46. The compound according to claim 1 which is HO—NH—CO—CH(CH₃)—CH(CH₂—CH(CH₃)₂)—CO—Nal—Ala—NH₂.

47. The compound according to claim 1 which is $$\text{HON}\overset{H}{\underset{}{-}}\text{COCH}_2-\underset{\underset{}{\overset{}{\diagdown}}}{\text{CH}}-\text{CO}-\text{Nal4(CH}_2\text{S)Ala}-\text{NH}_2.$$

48. The compound according to claim 1 which is HO—NH—CO—CH₂—CH(CH₂CH(CH₃)₂)—CONal—ψ(CH₂NH)—Ala—NH₂.

49. The compound according to claim 1 having the formula

<chemical structure showing HO-N(H)-C(=O)-CH₂-CH(iBu)-C(=O)-NH-CH(CH₂-naphthyl)-C(=O)-NH₂>

50. The compound according to claim 1 having the formula

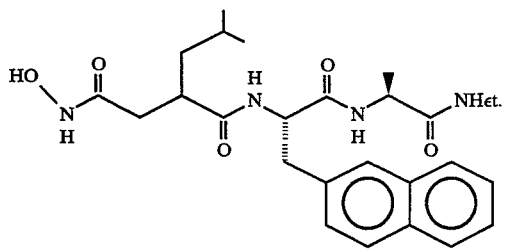

51. The compound according to claim 1 having the formula

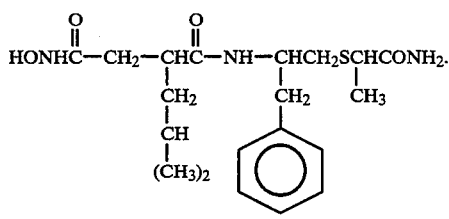

52. The compound according to claim 1 having the formula

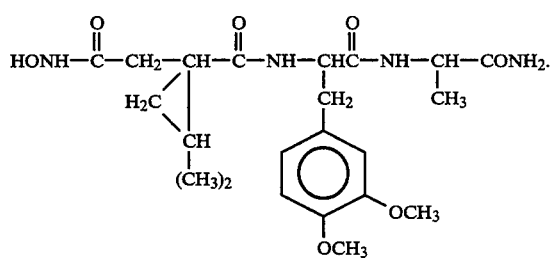

53. A pharmaceutical composition for the treatment of collagenase-related disorders which comprises an effective amount of a compound according to claim 1 and a pharmaceutical carrier therefor.

54. A method of treating a mammalian collagenase-related disorder which comprises administering to a mammal in need of treatment an inhibitory effective amount of a compound of claim 1.

55. The method of claim 54 wherein said mammalian collagenase-related disorder is rheumatoid arthritis.

56. The method of claim 54 wherein said mammalian collagenase-related disorder is periodontal disease.

57. The method of claim 54 wherein said mammalian collagenase-related disorder is corneal ulceration.

58. The method of claim 57 wherein said corneal ulceration is the result of alkali burning of the cornea.

59. The method of claim 57 wherein corneal ulceration is the result of said infectious keratisis.

60. The method of claim 59 wherein said infectious keratitis is induced by infection by *Pseudomonas aeruginosa*.

61. The method of claim 54 wherein said mammalian collagenase-related disorder is tumor metastasis.

62. A method of treating corneal ulceration resulting from infectious keratitis induced by infection by *Pseudomonas aeruginosa* comprising administering a corneal ulceration inhibiting amount of the compound of claim 1 to a mammal suffering from cornea ulceration resulting from infectious keratitis caused by infection by *Pseudomonas aeruginosa*.

63. A method of treating corneal ulceration resulting from alkali burning of the cornea comprising administering a cornea ulceration inhibiting amount of the compound of claim 1 to a mammal suffering from corneal ulceration resulting from alkali burning of the cornea.

64. The method according to claim 54 in which the callagenase related disorder is dermatitis.

65. The compound according to claim 1 in which $R_7$ is hydrogen, $R_2$ is aryl lower alkyl and B is $CH_2SO$, $CH_2SO_2$, $CH_2NH$, $COCH_2$, $CH=CH$ or

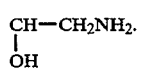

66. The compound according to claim 1 in which $R_7$ is hydrogen and $R_2$ is naphthylalanine, DOPA or DOPA $(OMe)_2$.

67. The compound according to claim 65 in which B is $CH_2S$, $CH_2SO_2$ or $CH_2NH_2$.

68. The compound according to claim 8 in which B is

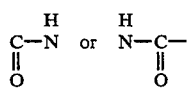

and X is a chemical bond and $R_2$ is

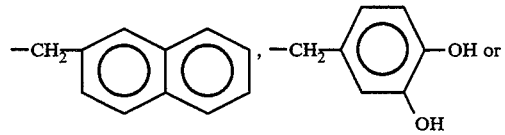

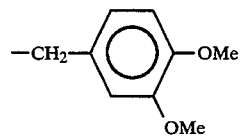

69. The compound according to claim 8 in which $R_7$ is hydrogen and

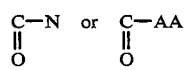

and X is

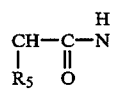

and $R_2$ is

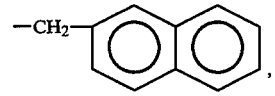

-continued

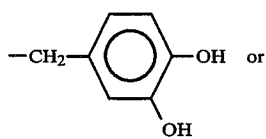

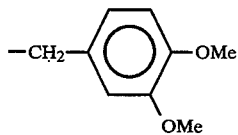

70. The compound according to claim 69 in which R₂ is

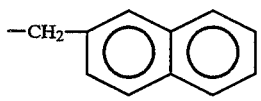

71. The pharmaceutical composition for the treatment of a disease caused by or made more severe by excess mammalian collagenase release which comprises a pharmaceutically effective amount of a compound according to claim 65 and a pharmaceutically acceptable carrier therefor.

72. The pharmaceutical composition for the treatment of a disease caused by or made more severe by excess mammalian collagenase release which comprises a pharmaceutically effective amount of a compound according to claim 66 and a pharmaceutically acceptable carrier therefor.

73. The pharmaceutical composition for the treatment of a disease caused by or made more severe by excess mammalian collagenase release which comprises a pharmaceutically effective amount of a compound according to claim 68 and a pharmaceutically acceptable carrier thereof.

74. The pharmaceutical composition for the treatment of a disease caused by or made more severe by excess mammalian collagenase release which comprises a pharmaceutically effective amount of a compound according to claim 69 and a pharmaceutically acceptable carrier therefor.

75. A method of treating a disease caused by or made more severe by excess mammalian collagenase release in a mammal which comprises administering to a mammal in need of such treatment an inhibiting effective amount of a compound according to claim 65.

76. A method of treating a disease caused by or made more severe by excess mammalian collagenase release in a mammal which comprises administering to a mammal in need of such treatment an inhibiting effective amount of a compound according to claim 66.

77. A method of treating a disease caused by or made more severe by excess mammalian collagenase release in a mammal which comprises administering to a mammal in need of such treatment an inhibiting effective amount of a compound according to claim 68.

78. A method of treating a disease caused by or made more severe by excess mammalian collagenase release in a mammal which comprises administering to a mammal in need of such treatment an inhibiting effective amount of a compound according to claim 69.

79. A method of treating ulceration of the cornea in a mammal which method comprises administering to a mammal in need of such treatment, an effective amount of a compound having the formula:

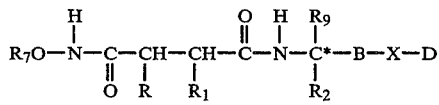

or pharmaceutically acceptable salts thereof wherein
$R_7$ is H,
$R_1$ and R are independently hydrogen or lower alkyl,
$R_2$ is aryl lower alkyl, said $R_2$ being unsubstituted or mono- or di-substituted with halo, nitro, carboxy, lower carbalkoxy, cyano, lower alkanoyl, trifluoromethyl, lower alkyl, hydroxy, lower alkoxy, formyl, amino, lower alkyl amino, di-lower alkyl amino, mercapto, lower alkylthio or mercapto lower alkyl,
B is

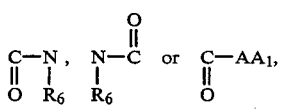

AA₂ is an amino acid residue,
X is a chemical bond, lower alkylene,

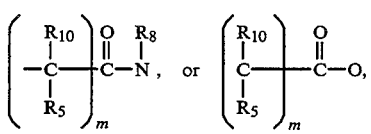

$R_{10}$ is methyl, ethyl or hydrogen,
m is 1,
$R_9$ is hydrogen,
$R_5$, $R_6$, and $R_8$ are independently hydrogen or lower alkyl,
D is hydrogen or lower alkyl which is unsubstituted or substituted with halo, nitro, carboxy, lower carbalkoxy, cyano, lower alkanoyl, trifluoromethyl, lower alkyl, hydroxy, lower alkoxy, formyl, amino, lower alkyl amino, dilower alkylamino, mercapto, lower alkyl thio, mercapto lower alkyl or aryl with the proviso that when B is

and X is a chemical bond or lower alkylene, then $R_2$ is not unsubstituted benzyl or monosubstituted with hydroxy or lower alkoxy and with the further proviso that when B is

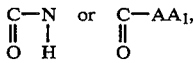

and X is

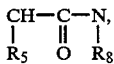

then R₂ is not unsubstituted benzyl or benzyl substituted with hydroxy or lower alkoxy.

80. The method according to claim 79 wherein R is H, R₁ is lower alkyl, and B is

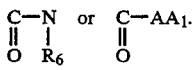

81. The method according to claim 79 wherein R₂ is bicycloarylalkylene.

82. The method according to claim 81 wherein R₂ is bicycloarylmethylene.

83. The method according to claim 82 wherein R₂ is

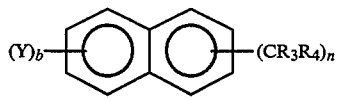

R₃ and R₄ are hydrogen and n is 1, b is 1 or 2, and Y is hydrogen, lower alkyl or lower alkoxy.

84. The method according to claim 83 wherein R₂ is naphthylmethylene.

85. The method according to claim 79 wherein
R₇ is H,
R is H,
R₁ is lower alkyl,
R₂ is

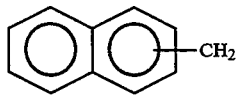

B is

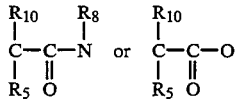

R₆ is hydrogen or lower alkyl and
AA₁ is an amino acid residue
X is a chemical bond

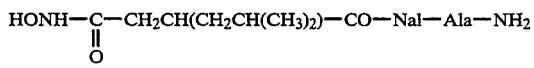

R₁₀ is hydrogen, methyl or ethyl and
D, R₅, R₆, and R₈ are independently hydrogen or lower alkyl.

86. The method according to claim 79 wherein the compound is

HO—NH—CO—CH(CH₃)—CH(CH₂—CH(CH₃)₂)—CO—Nal—Ala—NH₂,

HONH—C—CH₂CH(CH₂CH(CH₃)₂)—CO—Nal—Ala—NH₂
         ‖
         O

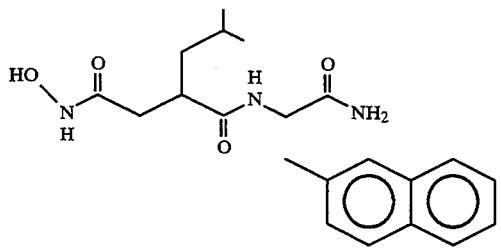

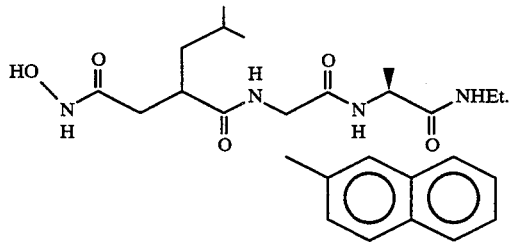

87. A pharmaceutical composition for the treatment of corneal ulceration which comprises a pharmaceutically effective amount of a compound

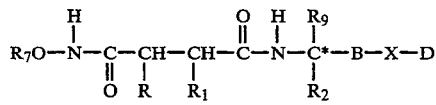

or pharmaceutically acceptable salts thereof wherein
R₇ is H,
R₁ and R are independently hydrogen or lower alkyl,
R₂ is aryl lower alkyl, said R₂ being unsubstituted or mono- or di-substituted with halo, nitro, carboxy, lower carbalkoxy, cyano, lower alkanoyl, trifluoromethyl, lower alkyl, hydroxy, lower alkoxy, formyl, amino, lower alkyl amino, di-lower alkyl amino, mercapto, lower alkylthio or mercapto lower alkyl,
B is

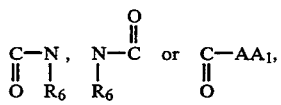

AA$_1$ is an amino acid residue,
X is a chemical bond, lower alkylene,
R$_9$ is hydrogen,

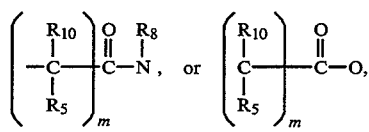

R$_{10}$ is methyl, ethyl or hydrogen,
m is 1,
R$_5$, R$_6$, and R$_8$ are independently hydrogen or lower alkyl,
D is hydrogen or lower alkyl which is unsubstituted or substituted with halo, nitro, carboxy, lower carbalkoxy, cyano, lower alkanoyl, trifluoromethyl, lower alkyl, hydroxy, lower alkoxy, formyl, amino, lower alkyl amino, diloweralkylamino, mercapto, lower alkyl thio, mercapto lower alkyl or aryl with the provisos that when B is

and X is a chemical bond or lower alkylene, then R$_2$ is not unsubstituted benzyl or benzyl monosubstituted with hydroxy or lower alkoxy and with the further proviso that when B is

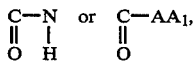

and X is

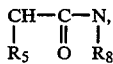

then R$_2$ is not unsubstituted benzyl or benzyl substituted with hydroxy or lower alkoxy.

88. The pharmaceutical composition according to claim 87 wherein R is H, R$_1$ is lower alkyl, and B is

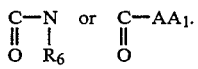

89. The pharmaceutical composition according to claim 87 wherein R$_2$ is bicycloarylalkylene.
90. The pharmaceutical composition according to claim 89 wherein R$_2$ is bicycloarylmethylene.
91. The pharmaceutical composition according to claim 90 wherein R$_2$ is

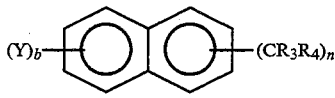

R$_3$ and R$_4$ are hydrogen and n is 1.
92. The pharmaceutical composition according to claim 91 wherein R$_2$ is naphthylmethylene.
93. The pharmaceutical composition according to claim 87 wherein
R$_7$ is H,
R is H,
R$_1$ is lower alkyl,
R$_1$ is

B is

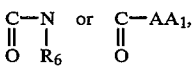

R$_6$ is hydrogen or lower alkyl,
AA$_1$ is an amino acid residue,
X is a chemical bond,

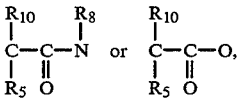

R$_{10}$ are independently hydrogen, methyl or ethyl, and
D, R$_5$, R$_6$, and R$_8$ are independently hydrogen or lower alkyl.
94. The pharmaceutical composition according to claim 87 wherein the compound is

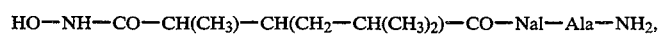

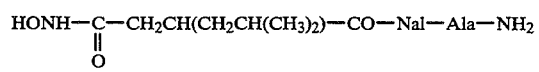

-continued

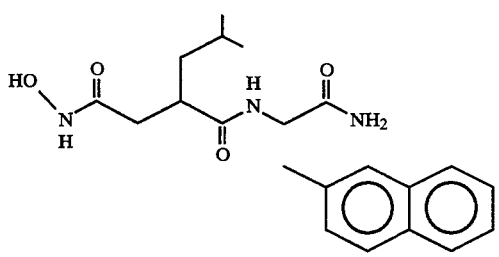

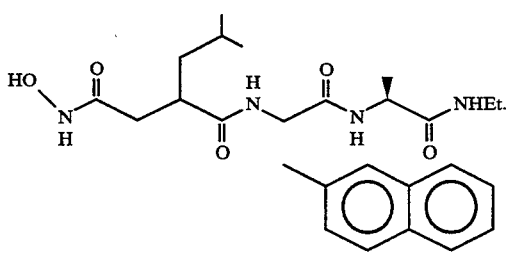

95. The pharmaceutical composition according to claim 87 wherein the composition is in solution.

96. The pharmaceutical composition according to claim 87 wherein the composition is in an isotonic solution.

97. The method of treating ulceration of the cornea in a mammal according to claim 79 which method comprises administering to a mammal in need of such treatment an effective amount of HO—NH—CO—CH$_2$—CH—(CH$_2$—CH(CH$_3$)$_2$)—CO—Nal—Pro—NH$_2$.

98. The pharmaceutical composition for the treatment of corneal ulceration according to to claim 87 comprising a pharmaceutically effective amount of a compound HO—NH—CO—CH$_2$—CH—(CH$_2$—CH(CH$_3$)$_2$) —CO—Nal—Pro—NH$_2$.

99. A compound of the formula

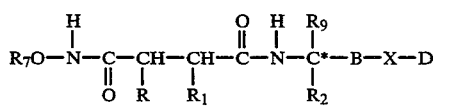

or pharmaceutically acceptable salts thereof wherein
R$_7$ is H,
R$_1$ and R are independently hydrogen or lower alkyl,
R$_2$ is aryl lower alkyl, said R$_2$ being unsubstituted or mono- or di-substituted with halo, nitro, carboxy, lower carbalkoxy, cyano, lower alkanoyl, trifluoromethyl, lower alkyl, hydroxy, lower alkoxy, formyl, amino, lower alkyl amino, di-lower alkyl amino, mercapto, lower alkylthio or mercapto lower alkyl,
R$_9$ is hydrogen,
B is

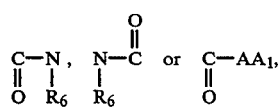

AA$_1$ is an amino acid residue,
X is a chemical bond, lower alkylene,

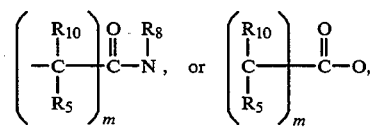

R$_{10}$ is methyl, ethyl or hydrogen,
m is 1,
R$_5$, R$_6$ and R$_8$ are independently hydrogen or lower alkyl;
D is hydrogen or lower alkyl which is unsubstituted or substituted with halo, nitro, carboxy, lower carbalkoxy, cyano, lower alkanoyl, trifluoromethyl, lower alkyl, hydroxy, lower alkoxy, formyl, amino, loweralkylamino, diloweralkylamino, mercapto, lower alkylthio, mercapto lower alkyl or aryl with the provisos that when B is

and X is a chemical bond or lower alkylene, then R$_2$ is not substituted benzyl or benzyl monosubstituted with hydroxy or lower alkoxy and with the further proviso that when B is

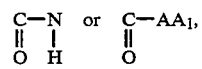

and X is

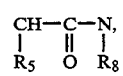

then R$_2$ is not unsubstituted benzyl or benzyl substituted with hydroxy or lower alkoxy.

100. The compound according to claim 99 wherein R is H, R$_1$ is lower alkyl, and B is

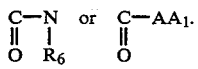

101. The compound according to claim 99 wherein $R_2$ is bicycloarylalkylene.

102. The compound according to claim 101 wherein $R_2$ is bicycloarylmethylene.

103. The compound according to claim 102 wherein $R_2$ is

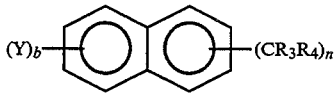

$R_3$ and $R_4$ are hydrogen and n is 1.

104. The compound according to claim 103 wherein $R_2$ is naphthylmethylene.

105. The compound according to claim 99 wherein
$R_7$ is H,
R is H,
$R_1$ is lower alkyl,
$R_2$ is

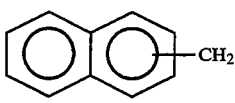

B is

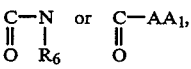

$R_6$ is hydrogen or lower alkyl,
$AA_1$ is an amino acid residue,
X is a chemical bond,

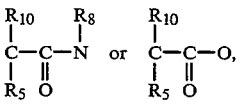

$R_{10}$ are independently hydrogen, methyl or ethyl, and
D, $R_5$, $R_6$, and $R_8$ are independently hydrogen or lower alkyl.

106. The compound according to claim 99 wherein $R_1$ is isobutyl, $R_2$ is naphthylmethylene, $R_9$ is hydrogen, $R_7$ is hydrogen, R is hydrogen, B is

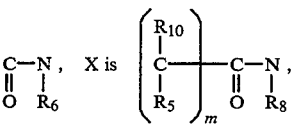

$R_6$ is hydrogen, $R_{10}$ is hydrogen, methyl, or ethyl, $R_5$ is hydrogen or lower alkyl, m is 1, $R_8$ is hydrogen, D is lower alkyl which is unsubstituted or substituted with amino, lower alkylamino or dilower alkylamino.

107. The compound according to claim 106 wherein $R_5$ is hydrogen, $R_{10}$ is methyl, and D is substituted ethyl, wherein the substituent is amino.

108. The compound according to claim 106 wherein D is ethyl which is substituted with amino, $R_2$ is 2-naphthylmethylene, $R_5$ is hydrogen and $R_{10}$ is methyl.

109. The sterioisomer of the compound claim 106 having the S configuration at each of the chiral centers.

110. The stereoisomer of the compound of claim 108 having the S configuration at each of the chiral centers.

111. A pharmaceutical composition comprising a pharmaceutically effective amount of a compound according to any one of claims 106–110.

112. A method of treating a disease in a mammal caused by or made more severe by mammalian collagenase which comprises administering to a mammal in need of such treatment an inhibiting effective amount of a compound according to any one of claims 106–110.

* * * * *

UNITED STATES PATENT AND TRADEMARK OFFICE
CERTIFICATE OF CORRECTION

PATENT NO. : 5,387,610  Page 1 of 4
DATED : February 7, 1995
INVENTOR(S) : Robert D. Gray, et al.

It is certified that error appears in the above-indentified patent and that said Letters Patent is hereby corrected as shown below:

Column 1, line 7, insert the following: --This invention was made with Government support under AR-39573 awarded by the National Institutes of Health. The Government has certain rights in the invention.--

Column 1, line 58: "or" should read --of--
Column 7, line 18: after "an" insert --aryl--
Column 8, line 21: "Lipine" should read --Lysine--
Column 11, line 67: "($H^3O$)" should read --($H^+$)--
Column 12, line 50: "O" should read --Q--
Column 14, line 15: delete "CH--COOH.--
Column 15, line 10: "al. <u>Tetrahderon</u>" should read --al. in <u>Tetrahedron</u>--
Column 18, line 68: "(CH3)" should read --(<u>C</u>H3)--
Column 20, line 7, "CH3" should read --<u>C</u>H3--
Column 20, line 12: "N <u>H</u>" should read --N<u>H</u>--
Column 20, line 63: "Aln" should read --Ala--
Column 21, line 62: "100%" should read --10%--
Column 23, line 22: "2H" should read --2N--

UNITED STATES PATENT AND TRADEMARK OFFICE
CERTIFICATE OF CORRECTION

PATENT NO. : 5,387,610
DATED : February 7, 1995
INVENTOR(S) : Robert D. Gray, et al.

It is certified that error appears in the above-indentified patent and that said Letters Patent is hereby corrected as shown below:

Column 24, line 15: before "94" insert --(--
Column 25, line 66: after ")." delete --C--
Column 27, lines 55-56: "2-car-bot" should read --2-carbo-t--
Column 30, line 21: "HCI" should read --HCl--
Column 32, lines 22 & 24: "Hal$_4$," should read --Hal$_\Psi$--
Column 32, line 23: (OMe)$_4$," should read --(OMe)$_\Psi$--
Column 32, lines 25 & 26: "Phe$_4$," should read --Phe$_\Psi$--
Column 35, line 62: "H4" should read --H$_\Psi$--
Column 35, lines 66 & 67: "Hal" should read --Nal--
Column 37, lines 6, 10, 15, 17, 19 & 22: "Hal" should read --Nal--

UNITED STATES PATENT AND TRADEMARK OFFICE
CERTIFICATE OF CORRECTION

PATENT NO. : 5,387,610
DATED : February 7, 1995
INVENTOR(S) : Robert D. Gray, et al.

It is certified that error appears in the above-indentified patent and that said Letters Patent is hereby corrected as shown below:

Column 37, lines 8, 21 & 27: "H4" should read --H$\Psi$--

Column 40, line 51, Claim 15: "claim 8" should read --claim 12--

Column 42, line 23, Claim 27: "$R_6$" should read --$R_8$--

Column 42, line 37, Claim 27: "$R_9$" should read --$R_8$--

Column 44, line 20, Claim 44: "CO-naphthyl-Nal" should read --CONal--

Column 44, line 45, Claim 47: "Nal4" should read --Nal$\Psi$--

Column 48, line 27, Claim 79: "$AA_2$" should read --$AA_1$--

Column 48, line 55, Claim 79: insert --benzyl-- before "monosubstituted"

UNITED STATES PATENT AND TRADEMARK OFFICE
CERTIFICATE OF CORRECTION

PATENT NO. : 5,387,610
DATED : February 7, 1995
INVENTOR(S) : Robert D. Gray, et al.

It is certified that error appears in the above-indentified patent and that said Letters Patent is hereby corrected as shown below:

Column 52, line 27, Claim 93: "$R_1$" should read --$R_2$--

Column 53, line 38, Claim 98: delete second occurrence of "to"

Signed and Sealed this

Twelfth Day of November, 1996

*Attest:*

BRUCE LEHMAN

*Attesting Officer*     *Commissioner of Patents and Trademarks*